(12) United States Patent
Lavold et al.

(10) Patent No.: US 9,150,610 B2
(45) Date of Patent: Oct. 6, 2015

(54) METHOD AND APPARATUS TO PERFORM HYDROGEN-DEUTERIUM EXCHANGE

(75) Inventors: Thorleif Lavold, Stockholm (SE); Juan Astorga Wells, Johanneshov (SE)

(73) Assignee: BIOMOTIF AB, Taby (SE)

( * ) Notice: Subject to any disclaimer, the term of this patent is extended or adjusted under 35 U.S.C. 154(b) by 42 days.

(21) Appl. No.: 13/510,099

(22) PCT Filed: Nov. 16, 2010

(86) PCT No.: PCT/SE2010/051264
§ 371 (c)(1),
(2), (4) Date: May 16, 2012

(87) PCT Pub. No.: WO2011/059401
PCT Pub. Date: May 19, 2011

(65) Prior Publication Data
US 2012/0231486 A1    Sep. 13, 2012

Related U.S. Application Data

(60) Provisional application No. 61/261,500, filed on Nov. 16, 2009, provisional application No. 61/261,911, filed on Nov. 17, 2009, provisional application No. 61/261,904, filed on Nov. 17, 2009.

(51) Int. Cl.
*G01N 27/26* (2006.01)
*G01N 30/04* (2006.01)
(Continued)

(52) U.S. Cl.
CPC *C07K 1/13* (2013.01); *G01N 30/06* (2013.01); *G01N 30/7266* (2013.01);
(Continued)

(58) Field of Classification Search
USPC .................................. 422/502; 435/23, 287.1
See application file for complete search history.

(56) References Cited

U.S. PATENT DOCUMENTS

| 4,687,644 | A |   | 8/1987  | Iniotakis et al. |         |
|-----------|---|---|---------|------------------|---------|
| 4,707,342 | A | * | 11/1987 | Iniotakis et al. | 423/248 |

(Continued)

FOREIGN PATENT DOCUMENTS

| WO | WO 2004/056697 A1 | 7/2004  |
|----|-------------------|---------|
| WO | WO 2008/125623 A3 | 10/2008 |

OTHER PUBLICATIONS

PCT International Search Report mailed Mar. 30, 2011 issued in a related PCT International Application No. PCT/SE2010/051264 (7 pages).

(Continued)

*Primary Examiner* — Jennifer Wecker
(74) *Attorney, Agent, or Firm* — Carter, DeLuca, Farrell & Schmidt, LLP; Robert P. Michal, Esq.

(57) ABSTRACT

Apparatus and methods to perform hydrogen/deuterium exchange using semipermeable membranes are described. The system has two channels separated by a semipermeable membrane. One channel comprises a flow carrying the analyte of interest, and the second channel comprises a solution comprising a deuterated solvent (e.g. deuterium oxide). The system does not require an external electric field gradient across the membrane to perform the hydrogen-deuterium exchange procedure. The present invention facilitates sample and reagent handling as well as simplifies manufacture of devices and/or instrumentation related to deuterium exchange.

Further described is a chemical analyzation device for analyzing chemical compositions and/or compounds, and a method for analyzing chemical compounds and a computer program product for inducing a computer to perform steps in the method. Also described is a method for analyzing interactions between analytes and charged molecules, and calculating binding coefficients of the analytes with respect to the charged molecules.

17 Claims, 23 Drawing Sheets

(51) Int. Cl.
*G01N 30/00* (2006.01)
*C07K 1/13* (2006.01)
*G01N 30/72* (2006.01)
*G01N 30/06* (2006.01)
*G06F 19/00* (2011.01)
*G01N 30/02* (2006.01)
*H01J 49/00* (2006.01)
*H01J 49/04* (2006.01)
*G01N 30/96* (2006.01)
*B01D 15/36* (2006.01)
*H01J 49/16* (2006.01)
*G01N 1/40* (2006.01)
*G01N 30/14* (2006.01)

(52) U.S. Cl.
CPC ........... *G06F 19/703* (2013.01); *B01D 15/361* (2013.01); *G01N 27/26* (2013.01); *G01N 30/00* (2013.01); *G01N 30/96* (2013.01); *G01N 2001/4011* (2013.01); *G01N 2001/4016* (2013.01); *G01N 2030/067* (2013.01); *G01N 2030/146* (2013.01); *H01J 49/00* (2013.01); *H01J 49/0018* (2013.01); *H01J 49/04* (2013.01); *H01J 49/0431* (2013.01); *H01J 49/165* (2013.01); *Y10T 436/24* (2015.01)

(56) References Cited

U.S. PATENT DOCUMENTS

| | | | |
|---|---|---|---|
| 4,952,126 A * | 8/1990 | Hanaoka et al. | 422/70 |
| 5,084,181 A | 1/1992 | Van Hook et al. | |
| 5,204,003 A | 4/1993 | Cochran, Jr. | |
| 5,492,838 A * | 2/1996 | Pawliszyn | 436/178 |
| 6,252,225 B1 | 6/2001 | Takada et al. | 250/288 |
| 6,332,914 B1 | 12/2001 | Lee | |
| 6,517,708 B1 * | 2/2003 | Patterson et al. | 210/96.2 |
| 6,949,741 B2 | 9/2005 | Cody et al. | |
| 2003/0017077 A1 * | 1/2003 | Hahn et al. | 422/81 |
| 2005/0284762 A1 * | 12/2005 | Astorga-Wells et al. | 204/451 |
| 2006/0166273 A1 | 7/2006 | Woods, Jr. et al. | |
| 2007/0187589 A1 * | 8/2007 | Cooks et al. | 250/288 |
| 2007/0224642 A1 * | 9/2007 | Emmett et al. | 435/7.1 |
| 2008/0019879 A1 * | 1/2008 | Schleifer | 422/102 |
| 2008/0047330 A1 * | 2/2008 | Whitehouse et al. | 73/61.48 |
| 2008/0311672 A1 * | 12/2008 | Dasgupta et al. | 436/161 |
| 2009/0020696 A1 * | 1/2009 | Bier | 250/288 |
| 2009/0095900 A1 * | 4/2009 | Whitehouse et al. | 250/282 |

OTHER PUBLICATIONS

PCT Written Opinion of the International Searching Authority mailed Mar. 30, 2011 issued in a related PCT International Application No. PCT/SE2010/051264 (10 pages).

Hansen et al, "Hydrogen/Deuterium Exchange of Hydrophobic Peptides in Model membranes by Electrospray Ionization Mass Spectrometry," Journal of the American Society for Mass Spectrometry, vol. 13, Issue 12, Dec. 2002, pp. 1376-1387 (12 pages).

Ryan T. Kelly et al., "Phase-Changing Sacrificial Materials for Interfacing Microfluidics with Ion-Permeable Membranes to Create On-Chip Preconcentrators and Electric Field Gradient Focusing Microchips," Analytical Chemistry, vol. 78, No. 8, Apr. 15, 2006, pp. 2565-2570 (DOI:10.1021/ac0521394).

Scott D. Noblitt et al., "Integrated Membrane Filters for Minimizing Hydrodynamic Flow and Filtering in Microfluidic Devices," Analytical Chemistry, vol. 79, No. 16, Aug. 15, 2007, pp. 6249-6254 (DOI:10.1021/ac0709431).

UKIPO Extended Search Report pursuant to Rule 62 EPC, the supplementary European search report (Art. 153(7) EPC) and the European search opinion (8 pages), Oct. 21, 2013.

X.Li, et al., Abstracts, Aug. 2009, (2 pages) 9$^{th}$ International Symposium, Mass Spectrometry in the Health & Life Sciences, San Francisco CA, Molecular & Cellular Proteomics, Vo. 8, No. 8 8 Suppl. 1, Aug. 2009 pp. S14-S15, XP055083806, American Society for Biochemistry and Molecular Biology. ISSN: 1535-9476, DOI; 10, 1074/mcp. S800408-MCP200.

Jingxi Pan, et al., Hydrogen/Deuterium Exchange Mass Spectrometry with Top-Down Electron Capture Dissociation for Characterizing Structural Transitions of a 17 kDa, Protein, Journal of the American Chemical Society, Aug. 11, 2009, (8 pages) vol. 131, No. 35, Deptartment of Chemistry, The University of Western Ontario, London ON, Canada and the University of Victoria-Genome BC Proteomics Centre, Victoria, BC, Canada.

* cited by examiner

| Flow rate (µL/min) | Observed mass (HDx cell deuteration) | Incorporated deuterons | % of maximum possible deuteration |
|---|---|---|---|
| 1.0 | 1582.4 | 12.8 | 91.4 |
| 0.8 | 1582.8 | 13.2 | 94.3 |
| 0.6 | 1582.9 | 13.4 | 95.6 |
| 0.4 | 1582.9 | 13.4 | 95.6 |

FIG 11

Fig 16
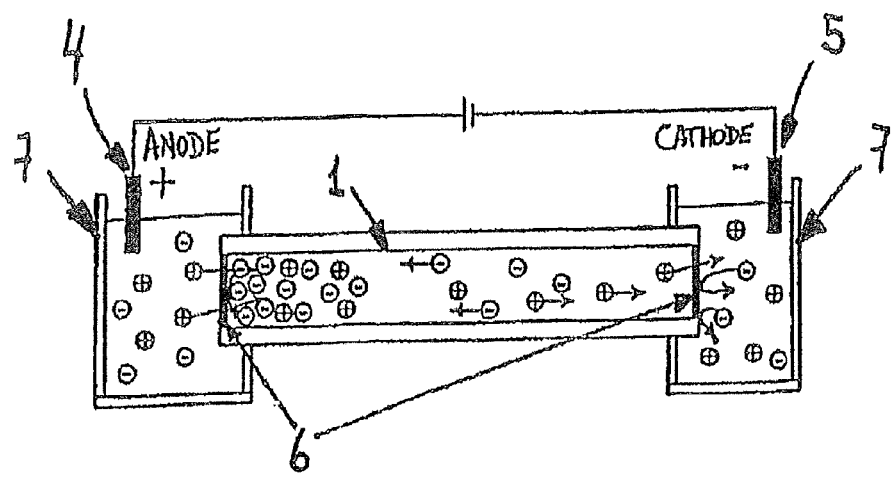
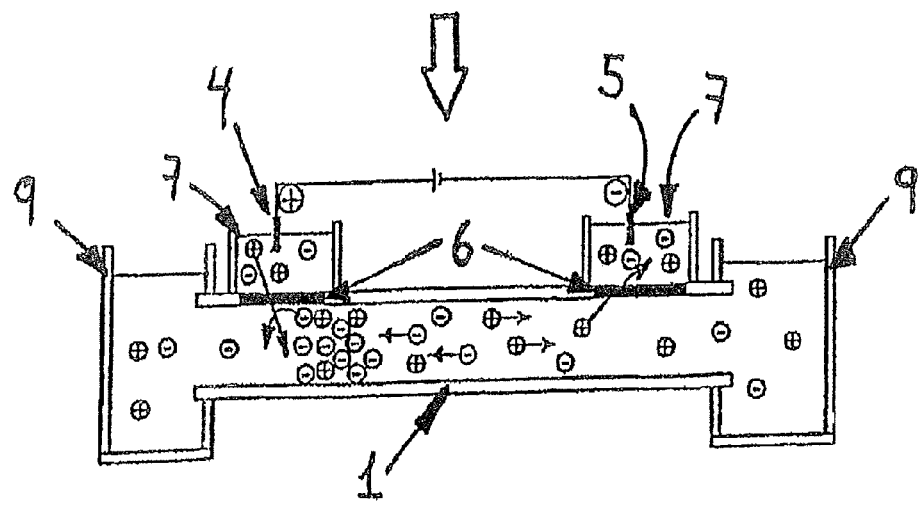

Fig 17
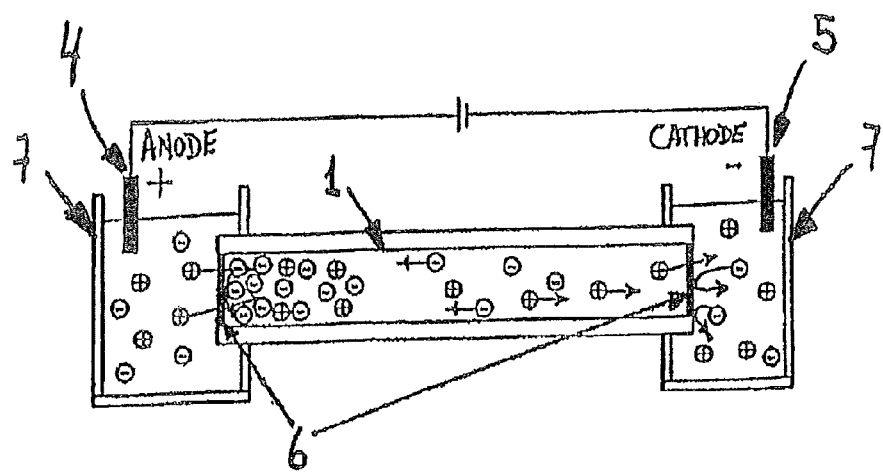
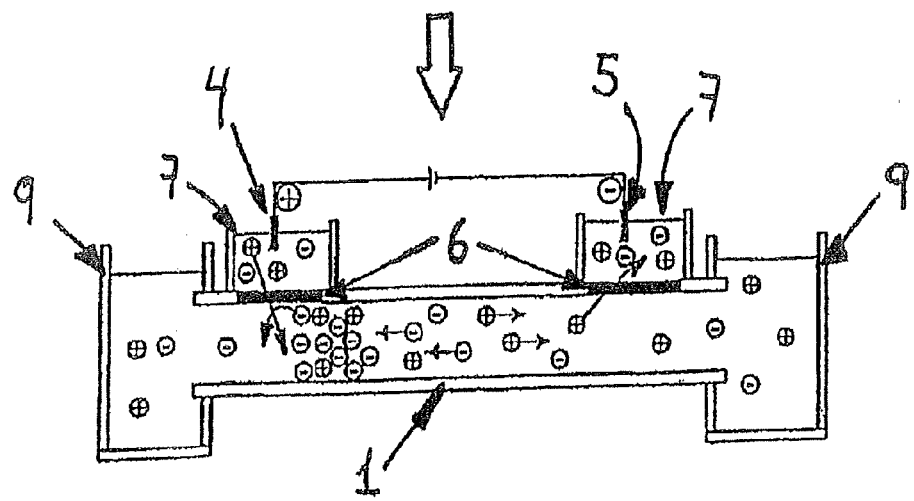

METHOD AND APPARATUS TO PERFORM HYDROGEN-DEUTERIUM EXCHANGE

CROSS-REFERENCE TO RELATED APPLICATIONS

This is a 371 national phase application of PCT International Application PCT/SE2010/051264 filed Nov. 16, 2010, which in turn claims benefit to U.S. provisional application Nos. 61/261,500 filed Nov. 16, 2009, 61/261,911 filed Nov. 17, 2009, and 61/261,904 filed Nov. 17, 2009, the entire disclosure of each of which is incorporated herein by reference.

FIELD OF INVENTION

This invention relates to the field of hydrogen/deuterium exchange in which an analyte comprising one or more exchangeable hydrogen(s) in its structure, it is exchanged into a deuteron by means of subjecting the analyte of interest to a deuterated solvent (e.g. deuterium oxide). The velocity and/or localization of the exchange can give structural and/or interactional and/or binding information about the analyte of interest.

The present invention further relates to a chemical analysation device, a method of chemical analysation, and a computer program product for chemical analysation.

The present invention further relates to a method for analyzing molecular interactions.

BACKGROUND

I. Some molecules have hydrogen atoms bound to their structure which—under some conditions—are continuously exchanged with hydrogen atoms present in the surrounding solvent (e.g. water). A typical example of this phenomenon is the hydrogen present at the amide group in the peptide bond. This particular amide hydrogen can be exchanged with other hydrogens present in the surrounding water. One characteristic of this phenomenon is that hydrogens present in peptide bonds more accessible to the water (e.g. those present in the in the surface of the protein) present faster exchange rates than those localized in the inner part of three-dimensional structure of the protein or belong to peptides bond where solvent accessibility is restricted by another protein and/or peptide and/or other portions of its three-dimensional structure. Now, if the solvent in which the protein is dissolved in changed from water (H2O) to deuterium oxide ($D_2O$), the protein will exchange its amide hydrogen for deuterium. Deuterium, also called heavy hydrogen, is a stable isotope of hydrogen. Even though deuterium presents some difference in its physico-chemical properties than hydrogen, proteins incorporate deuterium in their peptide bonds without significant disturbances in their structure and function. Because deuterium is heavier than hydrogen, the amount of deuterium incorporation into a polypeptide can be monitored by mass spectrometry. By measuring the amount of deuterium incorporated into the protein (e.g. deuterium incorporated versus incubation time), valuable information can be obtained about for example: protein/protein interactions, protein/drug interactions, protein/peptide interactions, protein/DNA interactions, protein/RNA interactions and peptide/peptide interactions.

When analyzing amide hydrogen exchange samples, some important technical issues need to be considered. Since after the exchange reaction, the sample is normally subjected to liquid chromatography or acidification using solvents containing water (H2O), the sample can easily reverse its deuteration state (the back change of deuterium to hydrogen) if the necessary precautions are taken. Because the exchange reaction is strongly pH dependent, the minimum exchange rate occurs at approximately pH 2.6 (for backbone amide hydrogen—or deuterium—of polypeptides). By performing the exchange at neutral pH and then rapidly drop the pH between 3 or 2, the back exchange rates of the deuterated polypeptides can be dramatically slowed, or quenched.

Hydrogen-deuterium exchange has taken an increasingly important role in drug development. Mapping the conformational changes of a target protein upon the binding of a ligand can accelerate the drug discovery pipeline by giving supplementary data to x-ray crystallography experiments for computational drug design. In addition, since hydrogen-deuterium exchange data gives information about conformational of the protein in solvent—and over time—, it is highly informative when combined with x-ray crystallography.

The following section describes the state-of-the art methodologies to perform hydrogen/deuterium exchange. The section only discusses technical issues relevant to the present invention. A detail explanation of the technique can be found in scientific literature. The aim of this section is to evaluate the differences and advantages of the present invention over the existing technologies. The advantages of the present invention over the state-of-the-art methodologies are explained on the "Description of the Invention" section. The state-of-the-art methodologies can be classified under the following groups:

1. Online Mixing of Target Molecule with Deuterated Solvent.

This system consists in mixing two flow streams using a T-connector. One flow stream carries the sample and the other carries the deuterated solvent (e.g. deuterium oxide). The exchange reaction starts as soon as both streams are mixed. The exchange reaction is analyzed by connecting the outlet of the system to electrospray ionization mass spectrometry and/or collecting the reaction products at the outlet of the system for further analysis. Using this method, the incubation time of the exchange reaction is inversely proportional to the overall flow rate of the system, thus deuteration level versus time graphs can be obtained using different flow rates. The main disadvantage of this approach is the necessary dilution of the sample in the deuterated solvent, since about 90 percent of total volume of reacting solution should correspond to the deuterated solvent. The later is an important problem, since the necessary dilution forces the user to utilize a high amount of sample for each analysis.

2. In-Tube Mixing of Target Molecule with Deuterated Solvent Followed by Reverse-Phase Liquid chromatography.

The sample is mixed with a deuterated solvent (e.g. deuterium oxide), and aliquots of the reaction are taken over time followed by online or off line mass spectrometry (e.g. 10 aliquots over a time period from 0 to 3 hrs). The laborious and meticulous nature of the sample-handling (in order to avoid back exchange) is the mayor drawback of this approach. Immediately after collection, the samples need to be mixed with acid (e.g. trifluoroacetic acid) in order to drop the pH to levels where the back exchange is minimized Additionally, directly after the acidification step samples are dipped in liquid nitrogen to promote rapid freezing to further minimize the back exchange. For analysis, samples are defrosted and quickly analyzed by online LC MS. Besides the labor-intensive characteristics of this technique, each step can potentially add errors to the reaction (e.g. lack of reproducibility in the collection-timing, acidification and froze/defrost procedures).

3. In-Tube Mixing of Target Molecule with Deuterated Solvent Followed by Pepsin Digestion and Reverse-Phase Liquid Chromatography.

This methodology is similar to the explained in the previous methodology (entitled: "In-tube mixing of target molecule with deuterated solvent followed by reverse-phase liquid chromatography"). In brief, the sample is mixed with a deuterated solvent (e.g. deuterium oxide), and aliquots of the reaction are taken at different times followed by acidification/freezing. After, posterior online pepsin digestion and reverse-phase chromatography (e.g. 10 aliquots over a time period from the beginning of the experiment to 3 hrs). This technique shares the same drawback from the previous paragraph (entitled: "In-tube mixing of target molecule with deuterated solvent followed by reverse-phase liquid chromatography"). Briefly, labor-intensive and potentially prompt to errors due to the many sample-handling steps (e.g. lack of reproducibility in the collection-timing, acidification and froze/defrost procedures).

Other Considerations.

An important characteristic shared by all the methodologies described above is the following. In order to obtain an efficient deuteration reaction, the target molecule needs to be dissolved in an excess of a given deuterated solvent (e.g. deuterium oxide). Now, since most of target molecules are dissolved in aqueous buffers (or pure water), the necessary dilution of the sample in the deuterated solvent—normally using dilution factors between 4 to 10 times—is detrimental for the overall sensitivity of the technique, requiring the use of a higher amount of sample per experiment.

II. Chemical analysis lies at the heart of modern science. Advances in analytical chemistry provide the scientific community with tools to advance in their respective research field, as from example in the drug development and pharmacokinetics, toxicology, diagnostics, environmental analysis, and in any other field were a chemical analysis is needed.

One powerful method of chemical analysis is mass spectrometry, in which ionized molecules or fragments thereof are analysed in order to obtain their mass-to-charge ratio based on their translational behaviour in an electric, magnetic or electromagnetic field. Various forms of mass spectrometers are known, such as quadrupole MS, quadrupole ion trap MS, time of flight MS, sector MS, and others. Depending on the method of ionization the molecule may undergo different amounts of fragmentation. By detecting ionized molecule or fragments thereof and comparing with databases on known molecules the chemist may be able to discern the identity of the molecule. For certain molecules however, there may be problems in that the fragment distributions may be very similar, so that it is almost impossible to guess at its identity.

In later years new methods of ionizations have been developed increasing the utility of MS. Most notably there has been developed ionization methods that lets the target molecule remain intact. One such method is APCI (atmospheric pressure chemical ionization), in which excited inert molecules are brought in contact with the target compound, so that the excitation energy ionizes the target. Examples of such ionization devices can be found in documents US 2007/0187589, and U.S. Pat. No. 6,949,741 which are hereby incorporated by reference. Another example can be found in "Design and Performance of a New Combination Electro Spray and Atmospheric Pressure Chemical Ionization Source", Victor V. Laiko and Craig M. Whitehouse, Proceedings of the 56th ASMS Conference on Mass Spectrometry and Allied Topics, Denver Colo., Jun. 1-5, 2008.

III. Molecular interaction studies are important in drug development and diagnostics as well as for the understanding of diseases at the molecular level. Most of the technologies utilized to investigate molecular interactions are based either on labeling of the target molecule (or the ligands) with a fluorescent dye, radioactive or UV/visible absorbing molecule or on attaching the target molecule to a solid surface, as in surface plasmon resonance or quartz crystal microbalance. The necessary modification of the target molecule (or ligand) and the blockade of the structure of the target molecule (or ligand) involved in linking it to the solid surface are the main problems of these technologies. First of all, the chemical modification of the target molecule (or ligand) has the potential to modify the interaction by giving false-positive binding, decreased or weaker binding or by totally suppressing the binding of the ligand. Also, the hiding or blocking of the molecular structures of the target molecule (or ligand) that are associated with the linkage onto the solid support has the potential to interfere with the normal interaction of the target molecule with the ligand.

Combinatorial chemistry is a technique by which large numbers of structurally distinct molecules may be synthesized at a time. The key of combinatorial chemistry is that a large range of analogues is synthesised using the same reaction conditions, in the same reaction vessels. In this way, the chemist can synthesise many hundreds or thousands of compounds in one time instead of preparing only a few by simple methodology. In its modern form, combinatorial chemistry has probably had its biggest impact in the pharmaceutical industry. Researchers attempting to optimize the activity profile of a compound create a "library" of many different but related compounds. Advances in robotics have led to an industrial approach to combinatorial synthesis, enabling companies to routinely produce over 100,000 new and unique compounds per year.

A challenge to the pharmaceutical industry is how to analyze such libraries comprising a vast number of compounds. Their potential interactions with target molecules of interest need to be analyzed as accurately and as early as possible in the research process.

SUMMARY OF THE INVENTION

I. The present invention relates to a method for performing hydrogen/deuterium exchange on analytes of interest comprising:

(a) providing at least one semipermeable membrane to separate at least one sample solution channel and at least one deuterated solution channel, wherein each said semipermeable membrane is arranged in a mixing region in order to allow the passage of deuterated solvent from a respective deuterated solution channel into a respective sample solution channel in order to promote the exchange of hydrogen atoms for deuterium atoms into the molecular structure of the analytes of interest traveling in said sample solution channel, (b) providing a flow stream of analytes of interest in at least a first sample solution channel in said mixing region and providing deuterated solvent in at least a first deuterated solution channel in said mixing region, (c) directing a portion of a population of analytes from said mixing region into a vacuum chamber; and (d) performing mass to charge analysis on a portion of said analytes transferred into said vacuum chamber.

According to one aspect of the invention, the method is characterized in that the analyte of interest subjected to deuteration is a protein and/or protein/protein complex and/or protein/drug complex and/or protein/DNA complex and/or protein/RNA and/or protein/carbohydrate complex and/or protein/lipid complex.

According to a preferred embodiment of the invention, the method further comprises digestion of the deuterated protein by a proteolytic enzyme prior to submission of the resulting deuterated proteolytic fragments to the mass to charge analysis, and by these means obtaining structural information about binding sites and/or secondary and/or tertiary and/or quaternary structural information about the protein.

The invention further relates to a system for performing hydrogen/deuterium exchange on analytes of interest comprising at least one sample solution channel separated by a semipermeable membrane from at least one deuterated solution channel, wherein said semipermeable membrane is arranged to allow the passage of said deuterated solvent from the deuterated solution channel into the sample solution channel in order to promote the exchange of hydrogen atoms for deuterium atoms into the molecular structure of the analytes of interest traveling in said sample solution channel, wherein said system further comprises means for directing a portion of said analyte population from said mixing region into a vacuum chamber; and means for conducting mass to charge analysis on a portion of said analytes transferred into said vacuum chamber.

II. One objective of the present invention is to indicate a device for improved analysis of a chemical sample with a higher probability of successful identification and/or quantification of a molecule.

According to one aspect of the invention this is achieved with a device according to claim 1. According to another aspect of the invention this is also achieved with a method according to claim 1.

The sample dividing member divides the sample into a first and a second part, so that the same sample may simultaneously be analysed twice and with different methods of analysis. Hence more information may become available for characterizing and/or quantifying the constituents in the sample. Also less time is needed for the analysis since both detectors may be run in parallel. Preferably the sample divider is arranged to divide the sample into two parts having nearly identical compositions and/or chemical proportions. Preferably the sample dividing member is arranged to divide the chemical sample so that the compositional ratios of the first and the second sample parts are identical to within 15%. Hence it is ensured that the two methods of analysis are made on similar samples, increasing the quality of the information obtained from the two analyses. Otherwise, it may be difficult or impossible to compare the results from the two detectors. Furthermore, the sample dividing member allows for a better control and less variation of the dividing ratios for a series of consecutive samples. By including a sample dividing member after the sample receiver, the sample is divided automatically by the device. The time for performing an experiment may then also decrease in relation to performing the two methods one after the other or on two different devices. The sample dividing member may therefore bring cost savings in for example labour costs. The sample dividing member may also divide a sample into more than two parts, such as three, four or more parts, alternatively, the device may comprise two or more sample dividing members.

According to one embodiment the chemical analysation device is arranged to carry the received sample in an undisrupted flow from the sample receiver to the detector. Preferably the chemical analysation device is arranged to conduct a flow of a carrier medium through the device, which carrier medium is adapted to convey the sample within or onto itself, and to transport the sample through the device. Thus an operator only needs to insert the sample into the sample receiver, and the chemical analysation device will then run automatically by itself.

According to one embodiment the device comprises a first ionizer for ionizing at least the compound to be analysed in the first sample, and the first detector comprises a mass spectrometer. A mass spectrometer measures the mass/charge of ionised substances and from the spectrum data the mass of a compound and/or its constituents may be discerned. Based on the data information may be acquired on the number and type of atoms forming the molecule or molecules in the sample, which is very important information when characterising a compound or a mixture of compounds. In order for a molecule to be analysed in a mass spectrometer the molecule needs to be charged, so that the molecule may be acted upon with electromagnetic forces. The charging of a compound may be performed by an ionizer several of which are known in the art.

According to one embodiment the first ionizer is a soft ionizer, which is arranged to ionize the compound to be analysed so that at least a majority of the ionized molecules of the compound to be analysed remain intact. Since the molecule remains intact the total molecular weight/charge of the molecule may be measured by the detector. Knowledge of the molecular weight is important in order to correctly determine the identity of a molecule. In particular, if the sample comprises a mixture of different compounds, it may be possible to determine the number of different compounds and their different molecular weights. During soft ionization the molecule may bond with one or more light ions or atoms to form a complex. One such complex may be a protonated target molecule in gas phase, [M+H$^+$], which may contribute with errors. Such a complex should still be considered an intact molecule in view of this application.

According to another embodiment the first ionizer is a hard ionizer, which is arranged to ionize the compound to be analysed so that at least a majority of the ionized molecules of the compound to be analysed are fragmented. In the second ionization a large molecule will thus break up into two or more smaller fragments, of which at least one is ionized so that it is charged. By breaking up the molecule its individual constituents are disclosed, wherein it may be easier to determine the inner structure of the molecule.

According to one embodiment the second detector is selected from the group consisting of electromagnetic radiation spectrometers, such as UV, IR, X-ray, and fluorescense; mass spectrometers, such as quadrupole MS, ion trap MS, sector MS, particle beam probe detectors, such as SEM, and ionization detectors, such as flame ionization detectors (FID). The second detector may provide additional information which may contribute to the analysation of the sample. A UV detector may provide quantitative information, and IR may provide structural or functional unit information and a beam probe detector may provide crystallographic information. According to one further embodiment the device may also comprise a third detector for providing even further information in one single experiment run on the device.

According to a preferred embodiment the chemical analysation device comprises a second ionizer and the second detector comprises a second mass spectrometer. Preferably, the second detector comprises a mass spectrometer selected from the group consisting of quadrupole mass spectrometers, ion trap mass spectrometers, and path mass spectrometers.

Preferably the first ionizer is a soft ionizer so that the molecule of the compound to be analysed remain intact, while the second ionizer is a hard ionizer, so that the molecule of the compound to be analysed is fragmented. By including both soft and hard ionizers in the same device, information of the molecule as a whole, but also information on its parts, such as functional groups, may be obtained with the same device. By combining the information on both the molecule as a whole and information on its fragments the probability of making a correct identification of an unknown molecule increases considerably.

According to one preferred embodiment the first detector comprises a time of flight mass spectrometer (TOF-MS). Preferably the time of flight mass spectrometer is furthermore connected with a soft ionizer. For high mass molecules the resolution of the mass spectrometer needs to be higher in order to properly separate between two peaks belonging to two different molecules. A time of flight mass spectrometer has a very high resolution, and may therefore more easily discern between two heavy molecules. Hence it is advantageous to connect a TOF-MS with the soft ionizer, which does not fragment the compound to be analysed.

Preferably the first mass spectrometer has a resolution of at least 3000 according to the full width half maximum definition. According to the FWHM method the resolution is given as $m/\Delta m$, where m is the measured m/z at the centre of a spectrum peak, and $\Delta m$ is measured as the width of a spectrum peak at 50% of its intensity. The higher the resolution the greater is the ability of the mass spectrometer to discern between two compounds having similar molecular weights. Preferably, the resolution of the first mass spectrometer is at least 5000. More preferably the resolution of the first mass spectrometer is at least 9000. This is needed to discriminate between large and heavy molecules with nearly identical weights. According to one embodiment the first mass spectrometer is a time of flight mass spectrometer, which are know to have high resolutions.

According to one embodiment the second detector comprises a mass spectrometer selected from the group consisting of quadrupole mass spectrometers, sector spectrometers, ion trap spectrometers and quadrupole ion trap spectrometers. Preferably the second mass spectrometer is connected with a hard ioniser. These mass spectrometers are less expensive, but also have less resolution. However, due to the fragmentation of the compound to be analysed the weight of the detected particles decreases so that the demands for resolution decrease as well. Another advantage of the hard ionizer coupled to a mass spectrometer in this group is that within the present state of technology the ratio of ionized molecules to non-ionized molecules for hard ionizers is known. Furthermore the transfer of the ionized molecules into the mass spectrometer may be performed without significant leakage, leading to that it is possible to quantify the amount and/or concentration of a molecule or its fragment when utilising the combination of a hard ionizer with any of these mass spectrometers.

According to one embodiment the device comprises a separator arranged to receive the sample from the sample receiver and to separate different compound within the sample from each other prior to delivering the sample to the sample dividing member. Hence the analysis of a sample comprising a mixture of compounds is simplified. By separating the compounds in the sample before the division of the sample it is ensured that the separation does not introduce differences between the first and the second sample parts.

According to one embodiment the separator separates compounds in the sample and delivers the compounds at different points of time to the sample dividing member. The sample dividing member may then divide each compound per se and further them to the ionizers and/or detectors. In case two or more compounds remain unseparated the first and the second sample parts will then still contain nearly equal proportions of the compounds at each point of time, so that correlation of the data obtained from the two detectors is simplified.

According to one embodiment the separator carries the sample within a continuous flow of a carrier medium. Preferably the first, second and/or third detectors are then adapted to receive a continuous flow of a carrier medium containing the sample. The sample dividing member is preferably arranged to divide the carrier medium into two sample parts. A continuous flow is advantageous since it is possible to analyse several compounds within a sample during a single experimental run. Preferably the separator comprises a chromatograph, such as a liquid chromatograph. In a most preferred embodiment the separator comprises a gas chromatograph. A gas chromatograph delivers a carrier medium in the form of a gas stream containing the sample, and is therefore easily divided into two or more sample parts. A compound within a gas stream may furthermore be easily ionized by ionizers of the present state of the art.

According to yet another aspect of the invention the objective is also achieved with a computer program product directly downloadable into the internal memory of a computer, the computer program product being adapted to be executed on the computer and to induce the computer to perform the following steps:

receiving a first set of measurement data from a first detector comprising a mass spectrometer, the data comprising information on mass/charge measured on a first sample part of a chemical sample, receiving a second set of measurement data from a second detector, the data comprising information acquired from measurements performed on a second sample part of the same chemical sample, fitting the first set of measurement data with information in a first database comprising a library with information on molecules and associated mass/charge values, fitting the second set of measurement data with information in a second database comprising a library with information on molecules and associated measurement values, and combining the results from the first and second fits to discern the identity, quantity, state and/or characteristics of at least one compound to be analysed within the chemical sample.

By receiving a first set of measurement data from a first detector comprising a mass spectrometer, the data comprising information on mass/charge measured on a first sample part of a chemical sample, and also receiving a second set of measurement data from a second detector, the data comprising information acquired from measurements performed on a second sample part of the same chemical sample, the computer program product may induce the computer to make a better analysis than when departing from measurement values of only one set of data of only one type.

By fitting the first set of measurement data with information in a first database comprising a library with information on molecules and associated mass/charge values, fitting the second set of measurement data with information in a second database comprising a library with information on molecules and associated measurement values, and then combining the results from the first and second fits to discern the identity, quantity, state and/or characteristics of at least one compound to be analysed within the chemical sample, much better results may be achieved.

According to one embodiment the computer program product is further adapted to induce the computer to perform the steps receiving a first set of measurement data from the first detector, the data comprising information acquired from measurements on molecules of the at least one compound to be analysed which were ionized by a first ionizer so that the ionized molecules remained intact, and receiving a second set of measurement data from the second detector, the data comprising information acquired from measurements on molecules of the at least one compound to be analysed which were ionized by a second ionizer so that the ionized molecules were fragmented. Thus the computer receives information on both the molecular weight of the intact molecule of the compound to be analysed and of its fragments. Preferably the computer program product is further adapted to induce the computer to perform the steps: fitting the first set of measurement data with information in a first database comprising a library with previously stored measurement values on intact molecules, fitting the second set of measurement data with information in a second database comprising a library with previously stored measurement values on molecular fragments, and combining the results from the first and second fits to increase the determining power when discerning the identity of the at least one compound to be analysed within the chemical sample. Thus the probability of a successful identification of a chemical compound may increase considerably.

III. The present invention further discloses a method for analyzing interactions between analytes and charged molecules and calculating binding coefficients of the analytes with respect to the charged molecules.

Figure 4A:
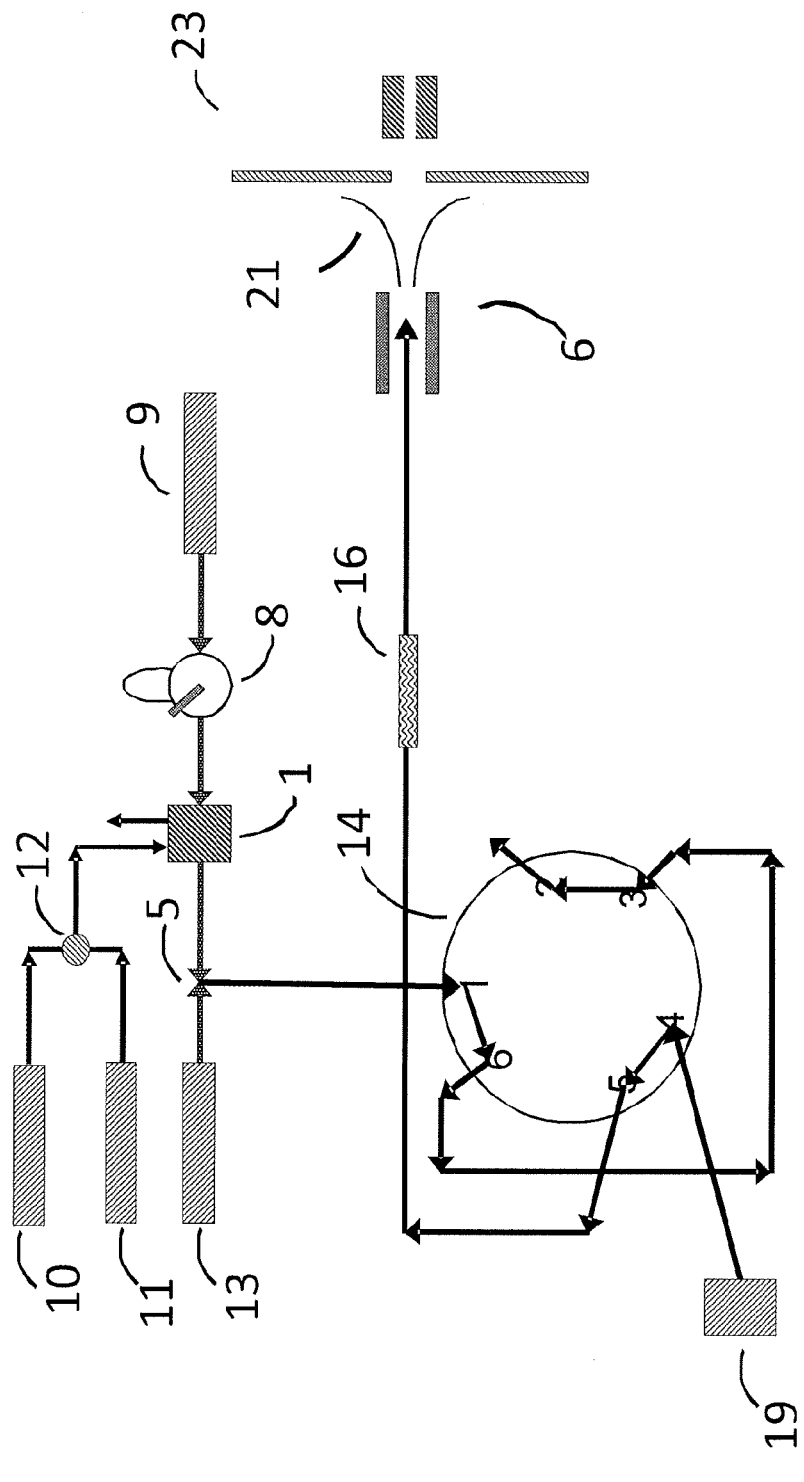
FIGS. 4A and 4B are diagrams of the deuteration cell coupled to sample injector, acidification, short chromatography column and online electrospray mass spectrometry with pneumatic nebulization. An injector 8 is connected to the deuteration cell 1. A pump 9 is connected to the injector 8 in a manner that allows the injection of discrete amount of sample (containing the analytes of interest) into the sample channel in the deuteration cell 1, where the hydrogen/deuterium exchange reaction can be performed. The solution infused into the second channel in the deuteration cell is pumped by the pumps 10 and/or 11, which are connected to the inlet of the second channel 4 by the tee-connector 12. The inlet of the second channel is labeled with number 24 and the exit with number 25. The outlet of the sample channel in the deuterator device 1 is connected to a tee channel configuration system 5 (or a tee-connector) in which the sample can be acidified, by mixing the sample solution with an acidified solution pumped into the tee-connector 5 by the pump 13. The outlet of the tee channel configuration system 5 is connected to a six-port valve 14 which allows the injection of discrete amount of the analytes of interest into the short chromatographic column 16. The outlet of the short chromatographic column 16 is connected to online electrospray mass spectrometry with pneumatic nebulization 6. After electrospray, 21, the ionized sample can enter into the mass spectrometer 23 (as seen in FIG. 4A)
Figure 4B:
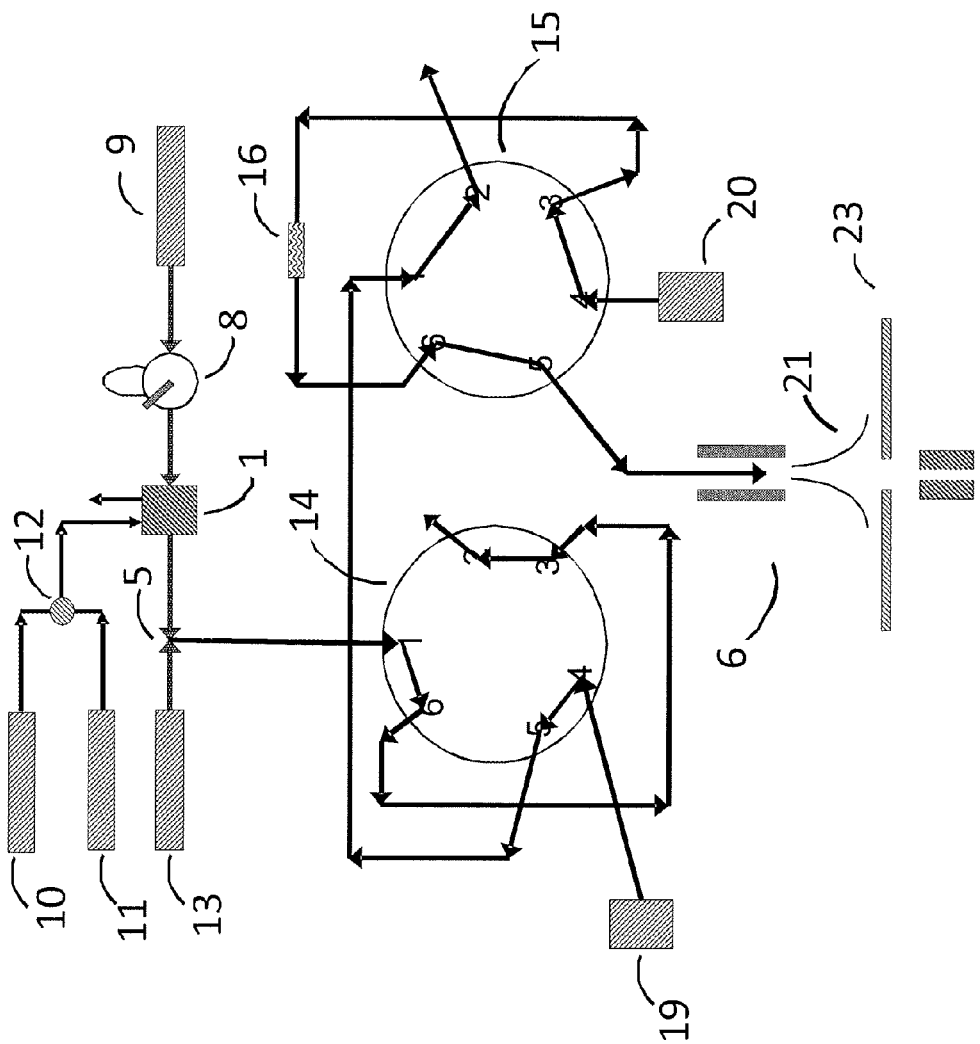

In another embodiment, shown in FIG. 4B, the six-port valve 14 is connected to the six-port valve 15 comprising the short chromatography column 16. The valves are configured in such a manner that the six-port valve 14 which allows the injection of discrete amount of the analytes of interest into the short chromatographic column 16 located at the six-port valve 15. One advantage of utilizing this setup is that the fluidic system situated upstream from the six-port valve 14 is isolated from the back pressure produced by the short chromatography column 16. Also, unwanted compounds that are separated by the short chromatography column 16 can be diverted to waste instead of being directed towards the mass spectrometer. After electrospray, 21, the ionized sample enters into the mass spectrometer 23.

Figure 5A:
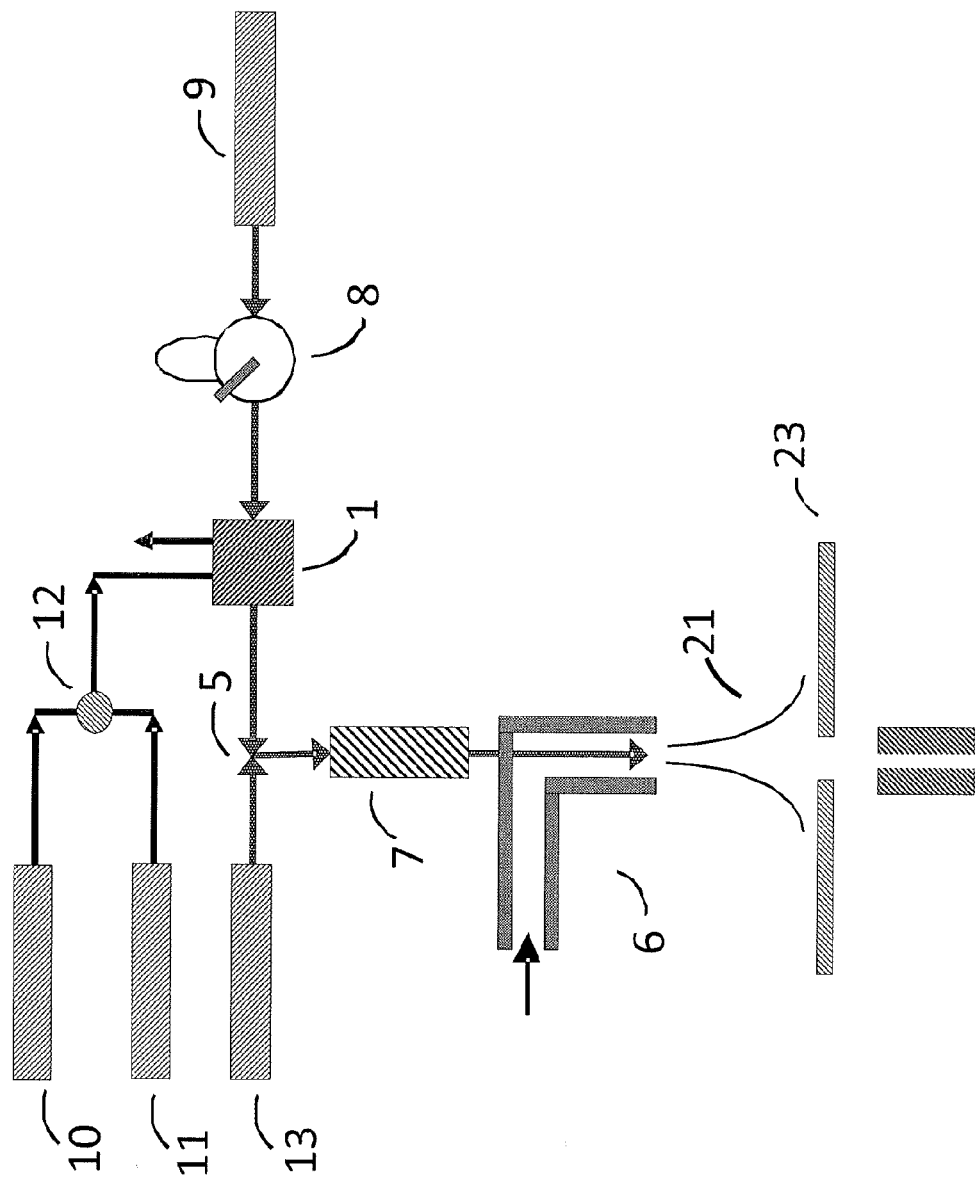
Figure 5B:
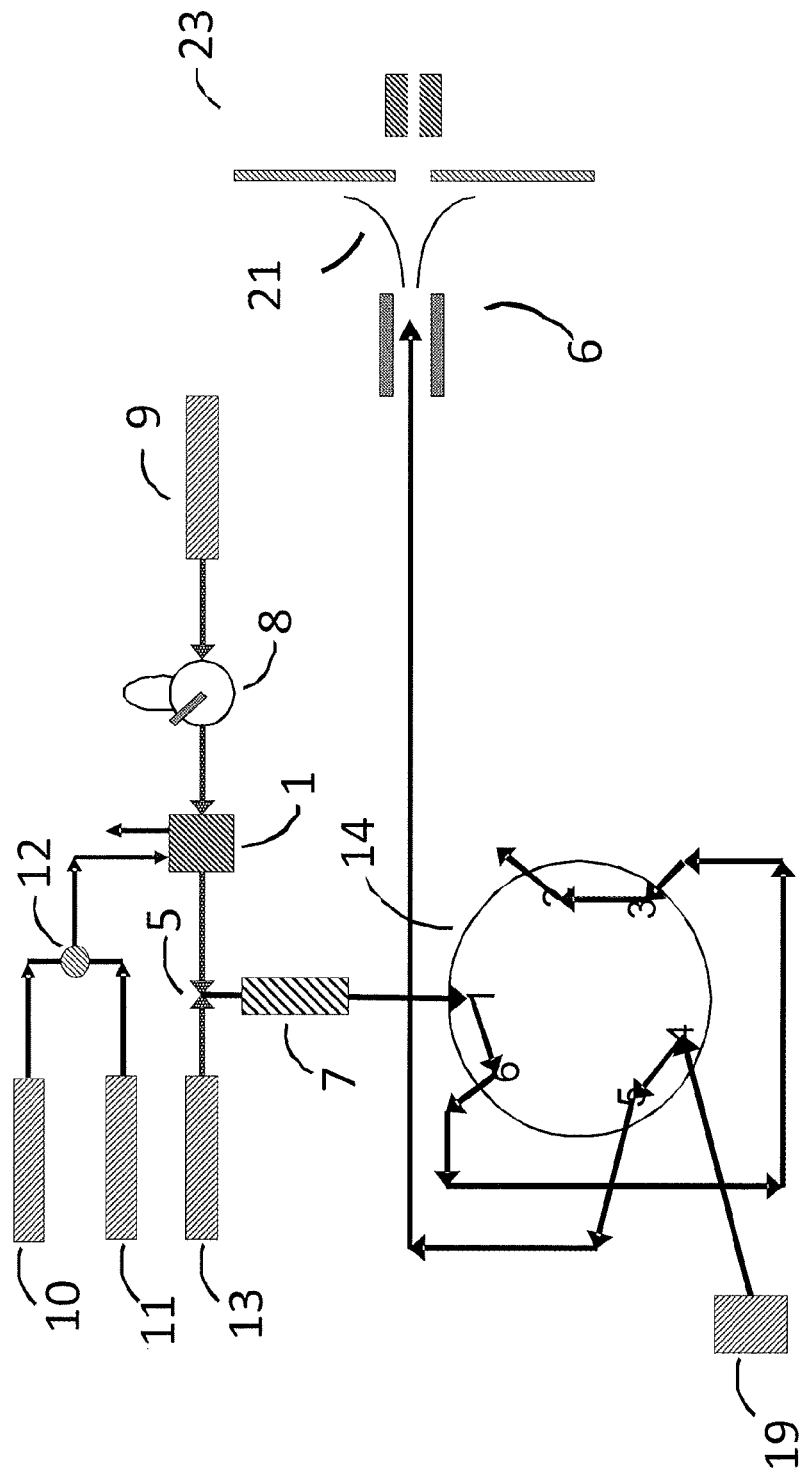

FIGS. 5A and 5B are diagrams of the deuteration cell coupled to sample injector, acidification, pepsin column and online electrospray mass spectrometry with pneumatic nebulization. An injector 8 is connected to the deuteration cell 1. A pump 9 is connected to the injector 8 in a manner that allows the injection of discrete amount of sample (containing the analytes of interest) into the sample channel in the deuteration cell 1, where the hydrogen/deuterium exchange reaction is performed. The solution infused into the second channel in the deuteration cell is pumped by the pumps 10 and/or 11, which are connected to the inlet of the second channel 4 by the tee-connector 12. The inlet of the second channel is labeled with number 24 and the exit with number 25. The outlet of the sample channel in the deuterator device 1 is connected to a tee channel configuration system 5 (or a tee-connector) in which the sample is acidified, by mixing the sample solution with an acidified solution pumped into the tee-connector 5 by the pump 13. The outlet of the tee channel configuration system 5 is connected to a pepsin column 7. The outlet of the pepsin column 7 can be connected to online electrospray mass spectrometry with pneumatic nebulization 6 (as seen in FIG. 5A). After electrospray, 21, the ionized sample enters into the mass spectrometer 23. In another configuration, shown in FIG. 5B, the pepsin column 7 is connected to the valve 14 (e.g. 6-port valve) in such a manner that allows the injection of discrete amounts of the digested sample into the online electrospray mass spectrometer with pneumatic nebulization 6. After electrospray, 21, the ionized sample can enter into the mass spectrometer 23.

Figure 6A:
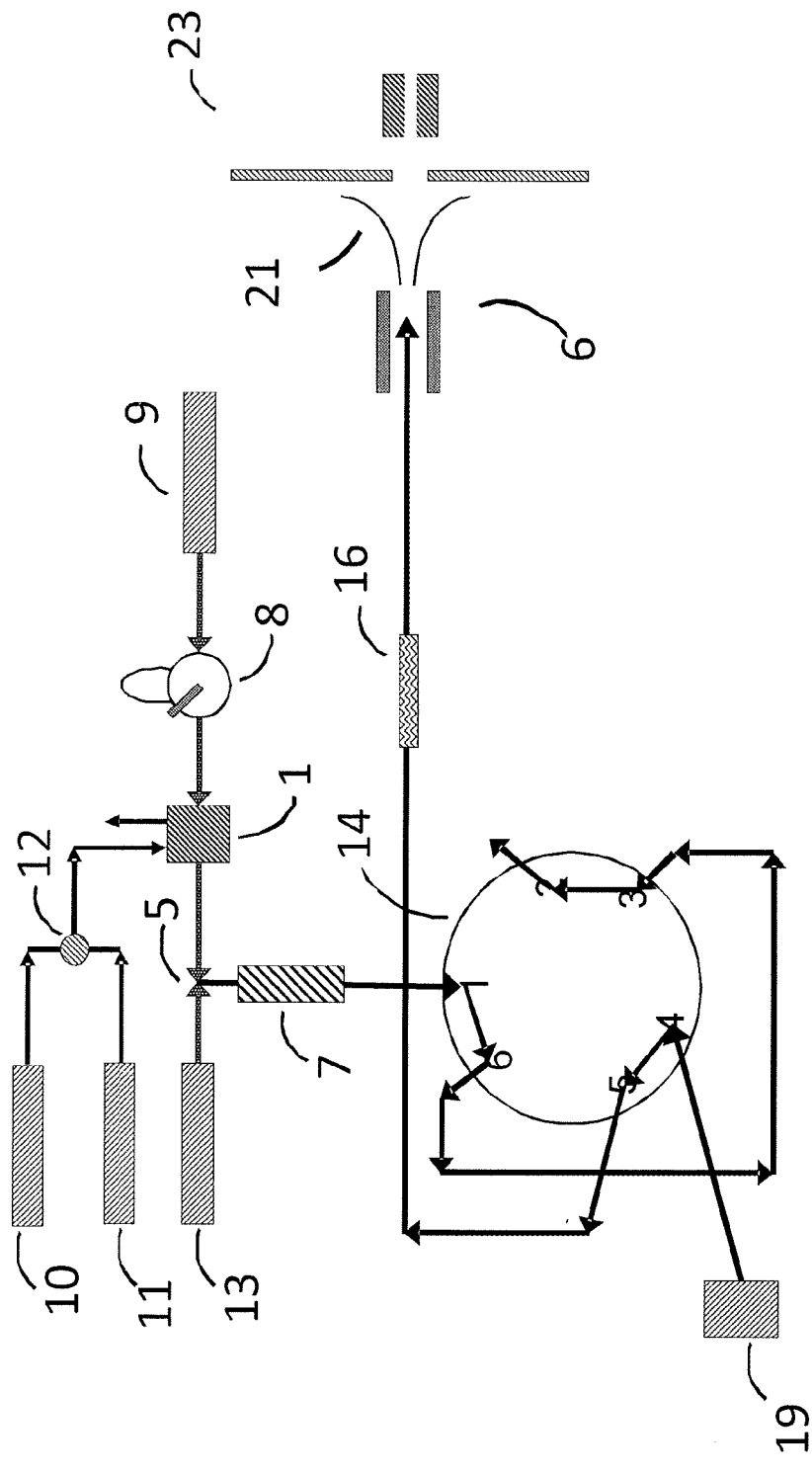
Figure 6B:
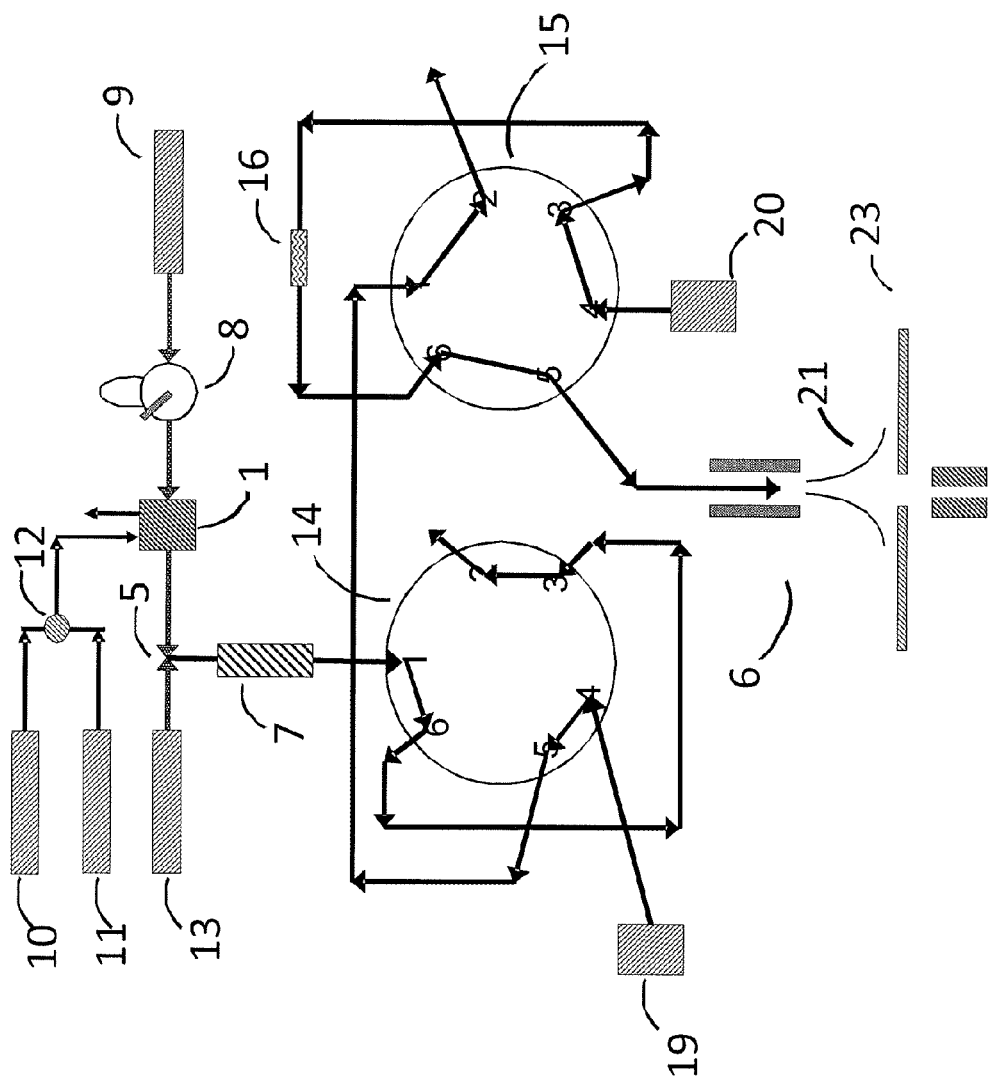
Figure 6C:
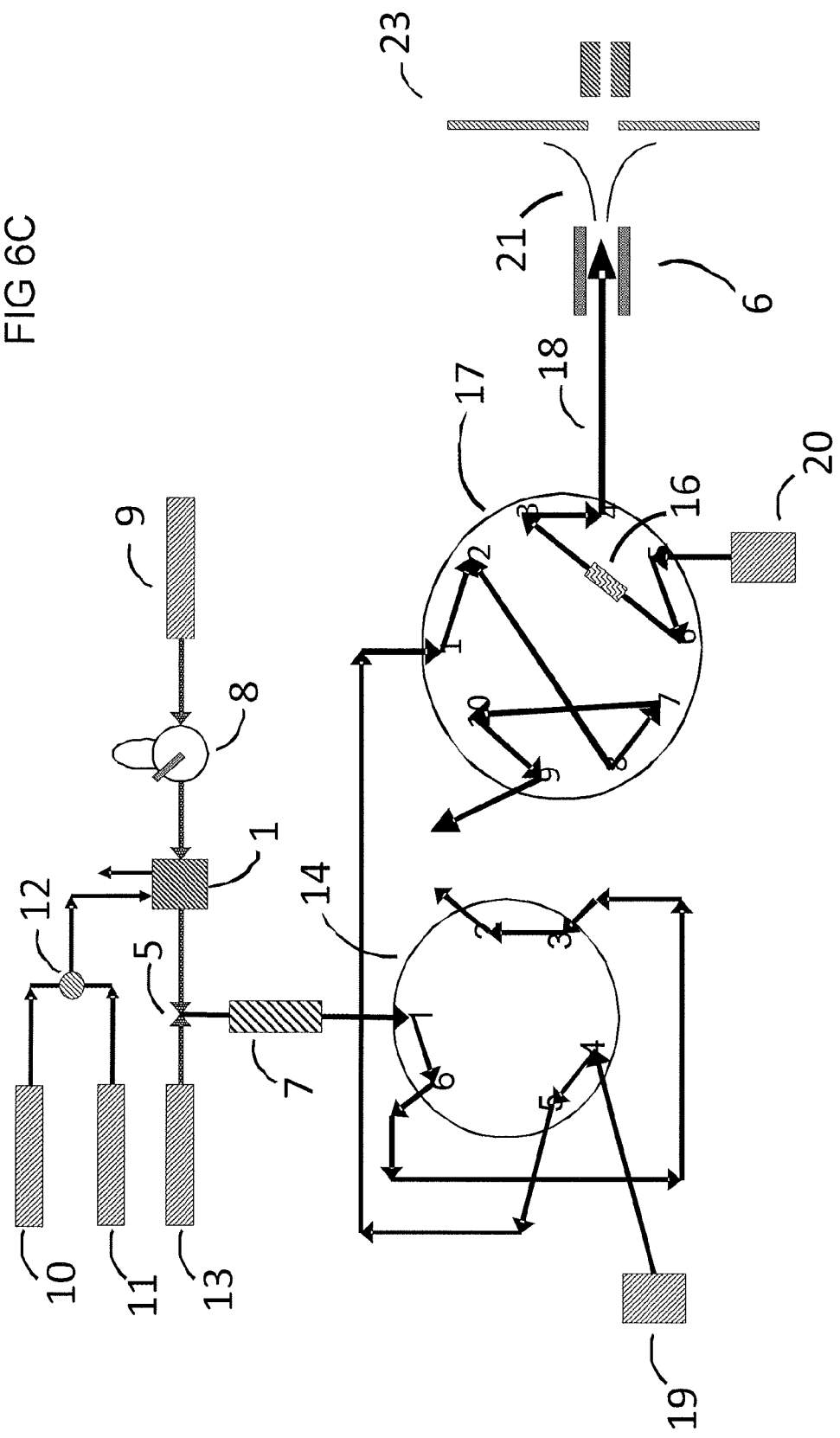

FIGS. 6A, 6B and 6C are diagrams of the deuteration cell coupled to sample injector, acidification, pepsin column, short chromatography column and online electrospray mass spectrometer with pneumatic nebulization. An injector 8 can be connected to the deuteration cell 1. A pump 9 can be connected to the injector 8 in a manner that allows the injection of discrete amount of sample (comprising the analytes of interest) into the sample channel in the deuteration cell 1, where the hydrogen/deuterium exchange reaction can be performed. The solution infused into the second channel in the deuteration cell can be pumped by the pumps 10 and/or 11, which can be connected to the inlet of the second channel 4 by the tee-connector 12. The inlet of the second channel is labeled with number 24 and the exit with number 25. The outlet of the sample channel in the deuterator device 1 can be connected to a tee channel configuration system 5 (or a tee-connector) in which the sample can be acidified, by mixing the sample solution with an acidified solution pumped into the tee-connector 5 by the pump 13. The outlet of the tee channel configuration system 5 can be connected to a pepsin column 7. The outlet of the pepsin column 7 can be connected to a six-port valve 14 which allows the injection of discrete amount of the pepsin digest into the short chromatography column 16, as shown in FIG. 6A. The outlet of the short chromatography column 16 can be connected to an online electrospray mass spectrometer with pneumatic nebulization 6. After electrospray, 21, the ionized sample can enter into the mass spectrometer 23. In another embodiment (as seen in FIG. 6), the six-port valve 14 can be connected to the six-port valve 15 which comprises the short chromatography column 16. The connection can be performed in such a manner that the valve 14 can inject discrete amount of the sample into the short chromatographic column 16. Finally, the valve 15 can be connected to an online electrospray mass spectrometer with pneumatic nebulization 6. After electrospray, 21, the ionized sample can enter into the mass spectrometer 23. One of the advantages of utilizing this setup is that all the system situated upstream from the pepsin column 7 can be isolated from the back pressure produced by the short chromatography column 16. Also, unwanted compounds that are separated by the short chromatography column 16 can be diverted to waste instead of being directed towards the mass spectrometer. Once the sample as been cleaned, the valve 16 can be switched to deliver the analyte of interest to the mass spectrometer. The outlet of the pepsin column 7 can be connected to an online electrospray mass spectrometer with pneumatic nebulization 6. After electrospray, 21, the ionized sample can enter into the mass spectrometer 23. In yet another configuration, the valve 14 can be connected to the ten port valve 17, which comprises the short chromatography column 16. The connection can be performed in such a manner that the valve 14 can inject discrete amount of the sample into the short chromatographic column 16 (located in the ten port valve 17). Finally, the ten port valve 17 can be connected to an online electrospray mass spectrometer with pneumatic nebulization 6. After electrospray, 21, the ionized sample can enter into the mass spectrometer 23. The advantage of the embodiment shown in FIG. 6C (over FIG. 6B) is that it can be easily modified, if required, to support an analytical column.

Figure 7A:
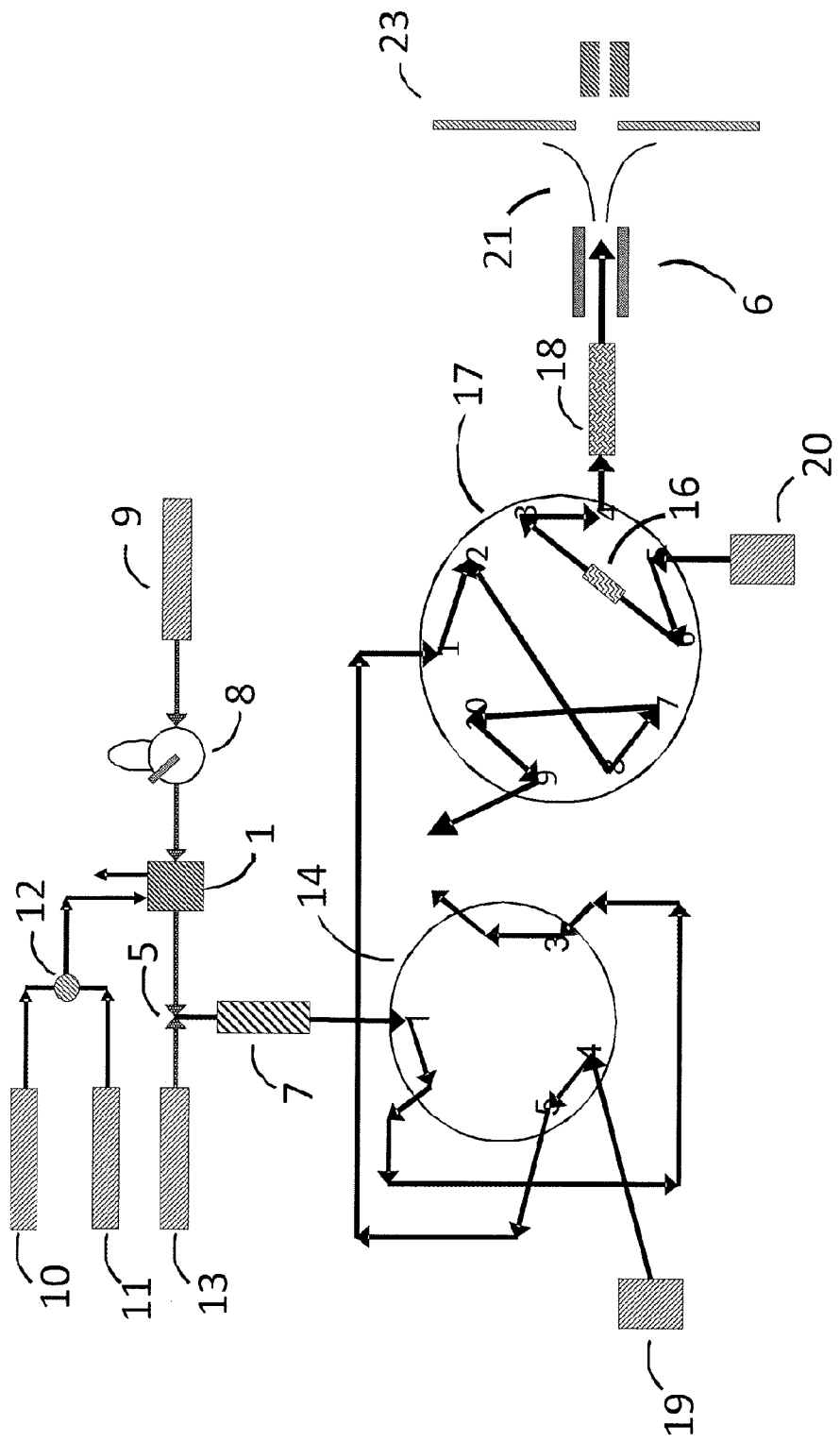
Figure 7B:
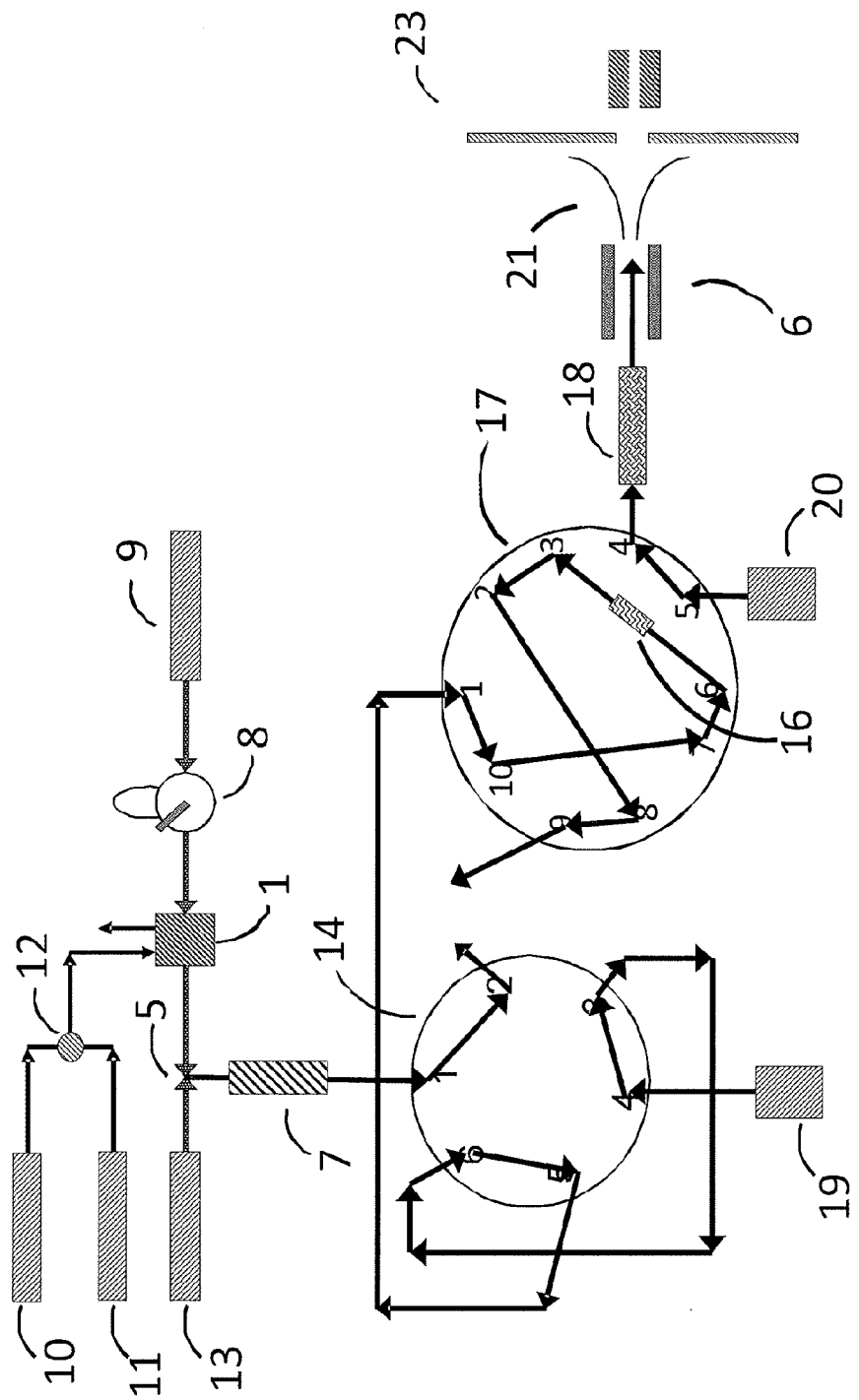

FIGS. 7A and 7B are diagrams of sample injector, online deuteration, acidification, pepsin column, short chromatography column, analytical chromatography column and ESI-MS. An injector 8 can be connected to the deuteration cell 1. A pump 9 can be connected to the injector 8 in a manner that allows the injection of discrete amount of sample (comprising the analytes of interest) into the sample channel in the deuteration cell 1, where the hydrogen/deuterium exchange reaction can be performed. The solution infused into the second channel in the deuteration cell can be pumped by the pumps 10 and/or 11, which can be connected to the inlet of the second channel 4 by the tee-connector 12. The inlet of the second channel is labeled with number 24 and the exit with number 25. The outlet of the sample channel in the deuterator device 1 can be connected to a tee channel configuration system 5 (or a tee-connector) in which the sample can be acidified, by mixing the sample solution with an acidified solution pumped into the tee-connector 5 by the pump 13. The outlet of the tee channel configuration system 5 can be connected to a pepsin column 7. The outlet of the pepsin column 7 can be connected to a six-port valve 14 which allows the injection of discrete amount of the pepsin digest into the ten-port valve 17 comprising the short chromatography column 16 and the analytical column 18. The embodiment using one six-port valve and one ten-port valve allows an efficient coupling of the pepsin column to two chromatographic columns, one short precolumn (C-8 or C-18) for concentration and/or desalting step, and another column, that serves as an analytical column to perform an efficient separation. After electrospray, 21, the ionized sample can enter into the mass spectrometer 23.

Figure 8:
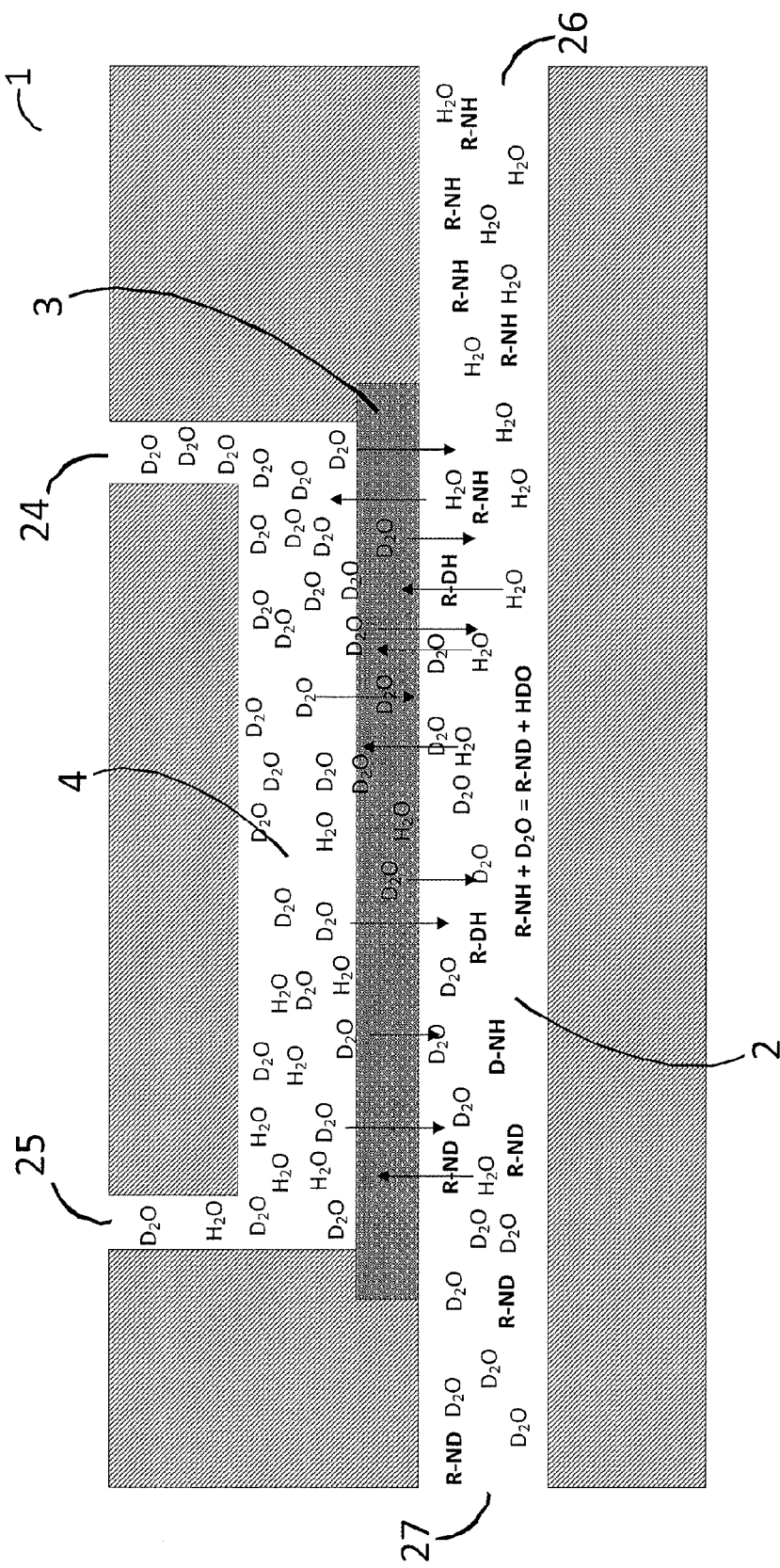

FIG. 8 is a diagram of representing the mechanism of deuteration procedure into the hydrogen/deuterium exchange cell. The R—NH symbols correspond to the undeuterated analyte of interest (with exchangeable amide hydrogen), R—ND corresponds to the deuterated analyte of interest, $H_2O$ corresponds to water and $D_2O$ corresponds to deuterium oxide. The deuteration cell 1 comprises two channels (channels 2 and 4), separated by the semipermeable membrane 3. The sample channel 2 comprises the flow carrying the analyte of interest, and it is separated by a semipermeable membrane 3 from the second channel 4 containing a water solution or deuterium oxide or another deuterated solvent. The solutions in the second channel 4 can be introduced via the inlet 24. The outlet of the second channel 4 is labeled with the number 25. The reaction R—NH+$D_2O$=R—ND+HDO represents the hydrogen/deuterium exchange reaction. The analytes of interest are injected into the cell via the inlet 26. The analytes of interest exit the cell by the outlet 27.

Figure 9:
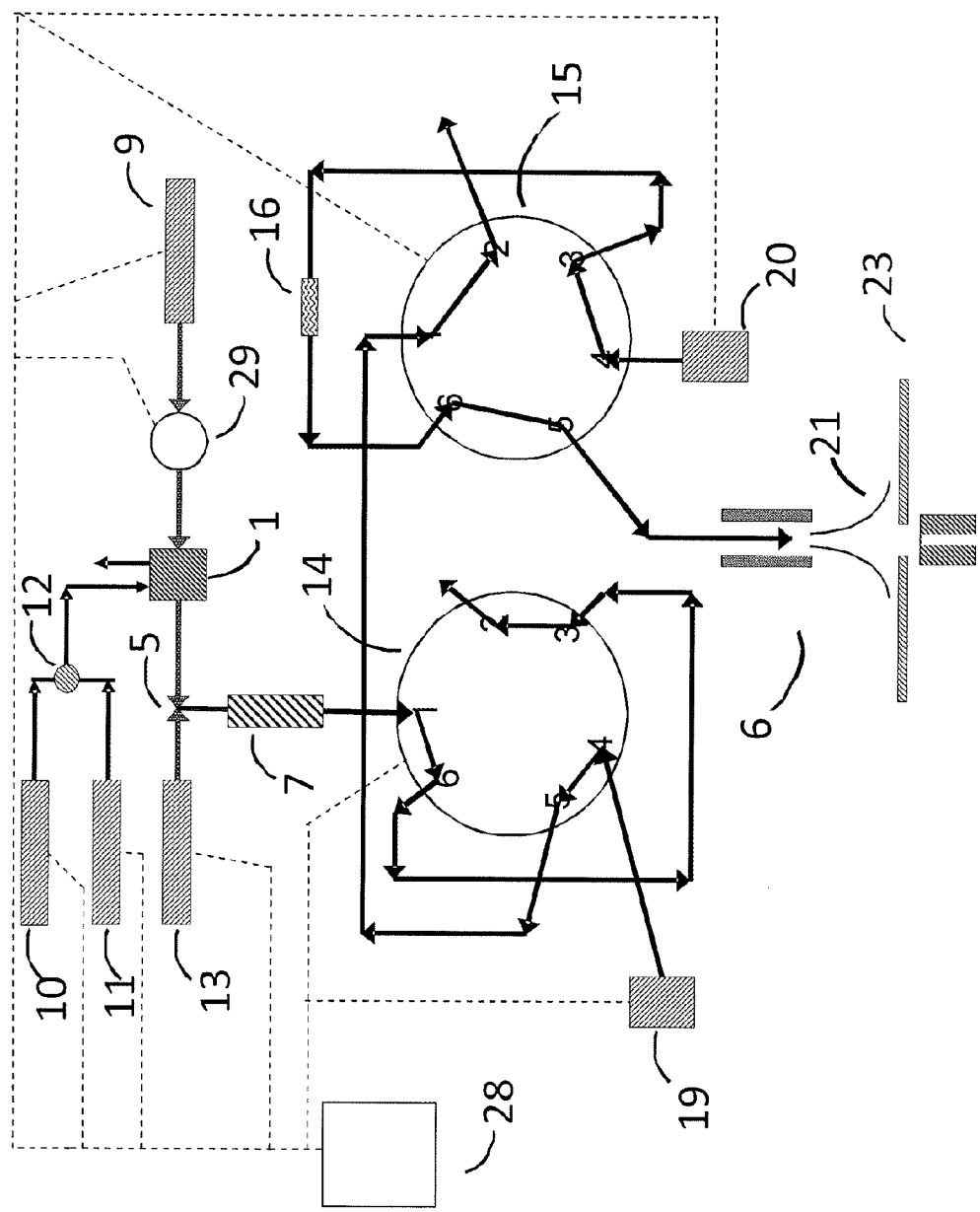

FIG. 9 is a diagram of an automated hydrogen/deuterium exchange instrument comprising an electronic controller 28, deuteration cell coupled to autoinjector injector, acidification, pepsin column, short chromatography column and an online electrospray mass spectrometer with pneumatic nebulization. An autoinjector 29 can be connected to the deuteration cell 1. A pump 9 can be connected to the autoinjector in a manner that allows the automated injection of discrete amount of sample (comprising the analytes of interest) into the sample channel in the deuteration cell 1, where the hydrogen/deuterium exchange reaction can be performed. The autoinjector 29 might correspond to a CTC PAL (CTC Analytics Switzerland) or others XYZ pipetting robots. Autoinjectors enable to collect samples from vials, add reagents, agitate, mix, heat, cool and inject the samples into the automated hydrogen/deuterium exchange instrument. The solution infused into the second channel in the deuteration cell can be pumped by the pumps 10 and/or 11, which can be connected to the inlet of the second channel 4 by the tee-connector 12. The outlet of the sample channel in the deuterator device 1 can be connected to a tee channel configuration system 5 (or a tee-connector) in which the sample can be acidified, by mixing the sample solution with an acidified solution pumped into the tee-connector 5 by the pump 13. The outlet of the tee channel configuration system 5 can be connected to a pepsin column 7. The outlet of the pepsin column 7 can be connected to a six-port valve 14 which allows the injection of discrete amount of the pepsin digest into the short chromatography column 16, as shown in FIG. 6A. The outlet of the short chromatography column 16 can be connected to an online electrospray mass spectrometer with pneumatic nebulization 6. After electrospray, 21, the ionized sample can enter into the mass spectrometer 23. In another embodiment (as seen in FIG. 6), the six-port valve 14 can be connected to the six-port valve 15 which comprises the short chromatography column 16. The connection can be performed in such a manner that the valve 14 can inject discrete amount of the sample into the short chromatographic column 16. Finally, the valve 15 can be connected to online electrospray mass spectrometry with pneumatic nebulization 6. After electrospray, 21, the ionized sample can enter into the mass spectrometer 23. The electronic controller 28 (an electric circuit board or a computer) can control in a coordinate manner the elements 9 and/or 10 and/or 11 and/or 13 and/or 14 and/or 15 and/or 19 and/or 20 and/or 29 as well as might coordinate and/or control the mass spectrometrical analysis. Dashed lines depict the electrical connection and/or wireless communication pathways that an automated system might need for automated (non limited example).

Figure 10:
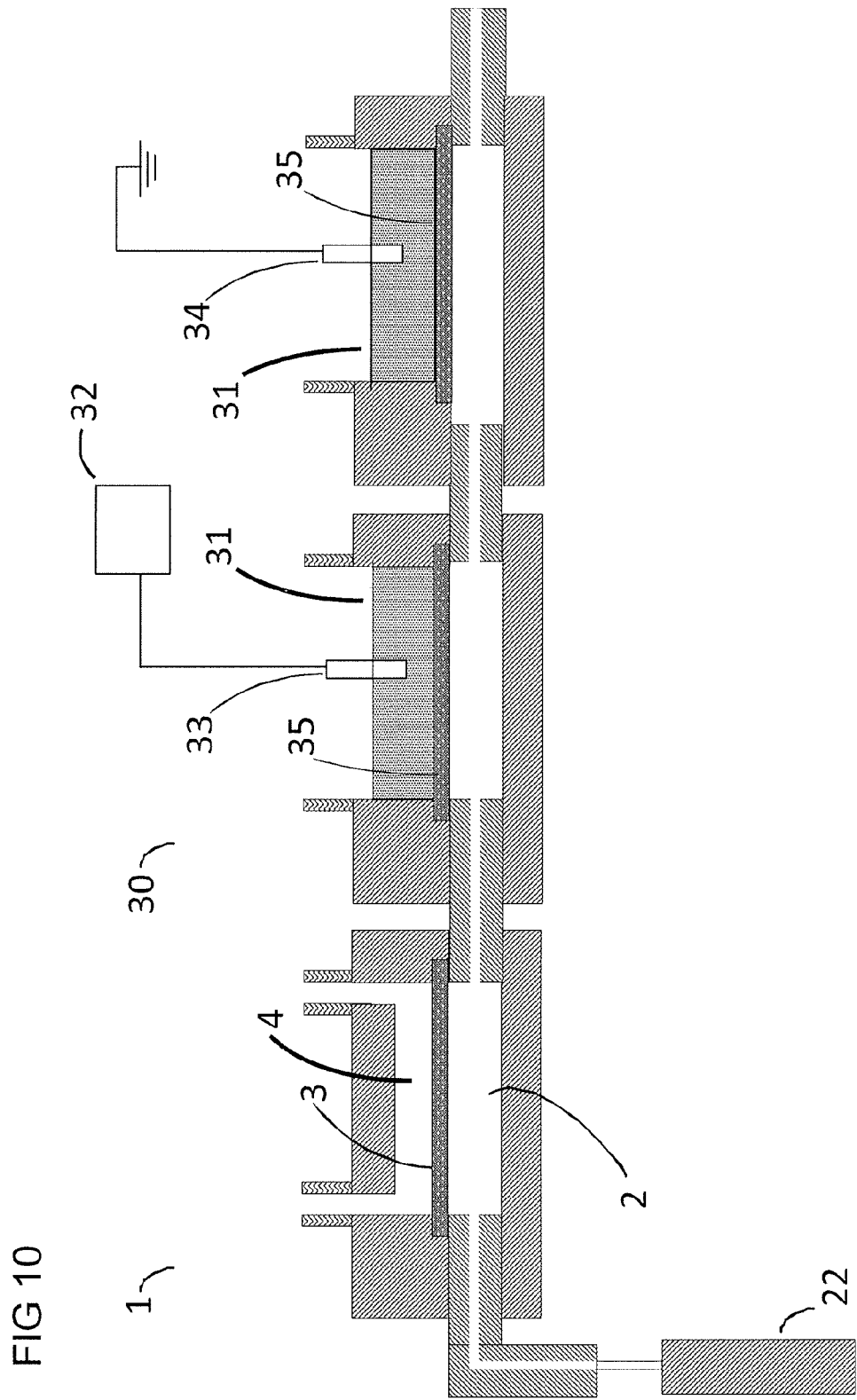

FIG. 10 is a diagram of a hydrogen/deuterium exchange cell coupled to an electrocapture system, where the out let of the hydrogen/deuterium exchange cell 1 can be connected to an electrocapture system 30. The electrocapture system comprises two electrolyte reservoirs 31 which have electrodes 33 and 34 and semipermeable membranes 35 that separate the electrodes 33 and 34 from the sample channel 2. The power supply 32 produces an electrical field between the electrodes 34 and 34, which can capture charged molecules in the channel 2 when said molecules enter into the electrocapture system 30.

FIG. 11 corresponds to hydrogen/deuterium exchange data produced by the present invention allowing on-line deuteration of [Glu1]-Fibrinopeptide B at different flow rates. The data is compared against off-line deuteration (direct dilution with deuterium oxide).

Figure 12:
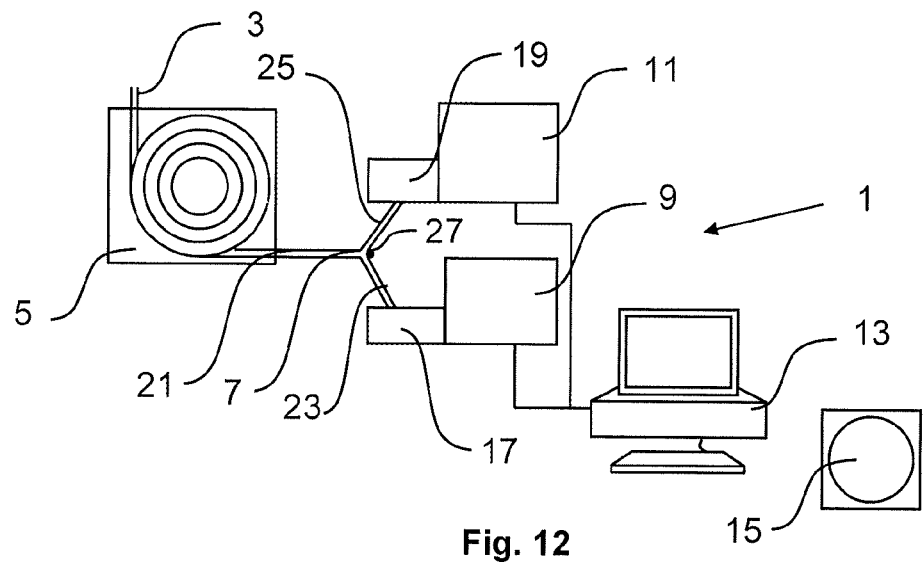

FIG. 12 shows a first example of a chemical analysation device according to one aspect of the invention.

Figure 13:
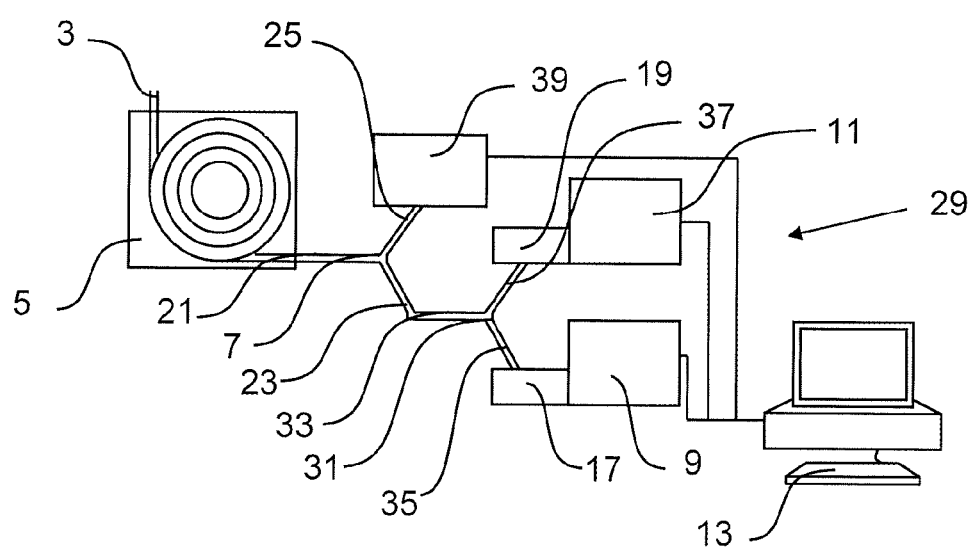

FIG. 13 shows a second example of a chemical analysation device according to another aspect of the invention.

FIGS. 14a-d show different examples of sample dividing members according to an aspect of the invention.

Figure 15:
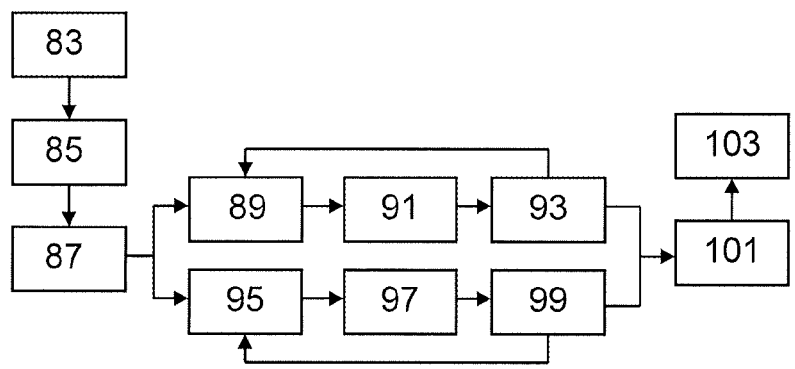

FIG. 15 shows one example of a method according to yet another aspect of the invention.

FIG. 16A-B is a schematic diagram of a hypothetical device for creating areas of different ionic concentrations in an electrophoretic channel. Ion-selective membranes (6) are placed between the electrodes (4, 5) and the electrophoretic channel (1). Said membranes do not permit the normal circulation of particular ions towards their respective electrodes creating zones with different ionic concentration. In FIG. 16A, the ends of an electrophoretic channel are sealed with cation selective membranes and positioned into electrolyte reservoirs (7) in a close-channel configuration. FIG. 16B illustrates an open-channel design, where the solution in the buffer reservoirs (9) can be freely circulated in the electrophoretic channel, but having the same electrical properties as in FIG. 16A.

FIG. 17A-B is a schematic diagram of a hypothetical device for creating a discontinuous zone in a continuous flowing stream. A hydrodynamic flow is applied to the electrophoretic channel (1), wherein the two zones of different ionic strength and electric field are created. FIG. 17A illustrates the movement of ions across the electrophoretic channel. FIG. 17B illustrates the position of the created zones with different electric field strength.

Figure 18:
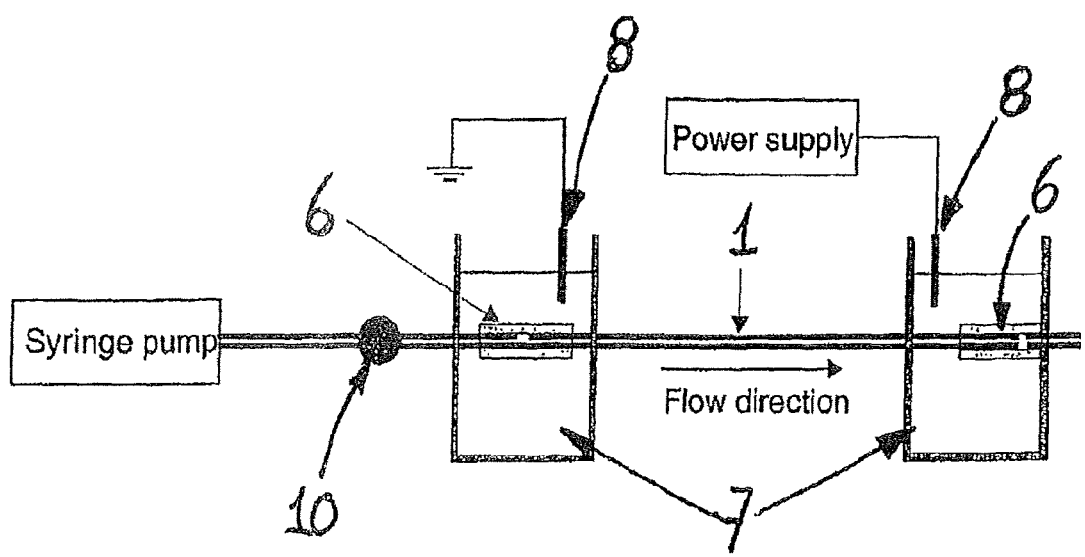

FIG. 18 is a schematic representation of a microfluidic electrocapture device. The device has the same characteristics as in FIG. 17. A valve (10) connects the microfluidic device with a syringe pump that produces a hydrodynamic flow. Electrodes (8) positioned into electrolyte reservoirs (7) serve as a cathode or anode depending on polarity of the electric potential applied by power supply.

Figure 19A:
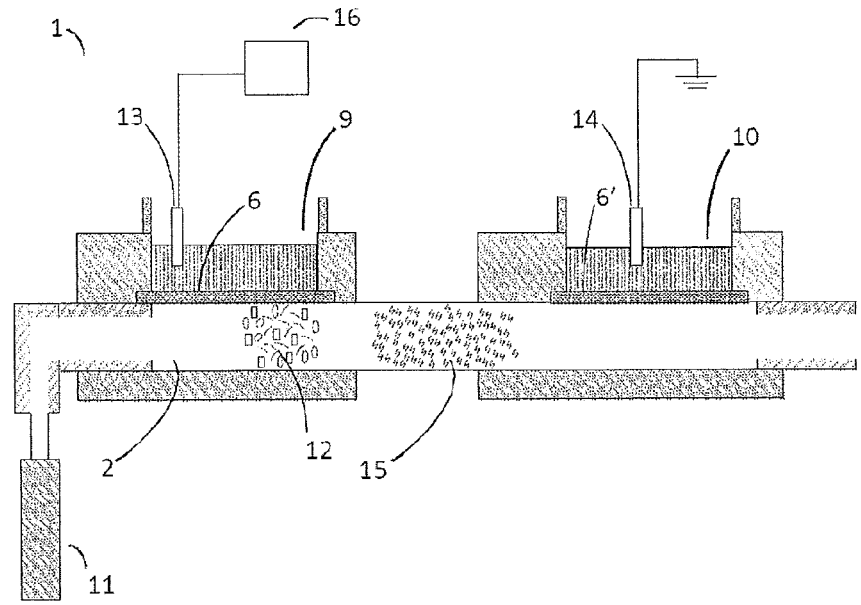
Figure 19B:
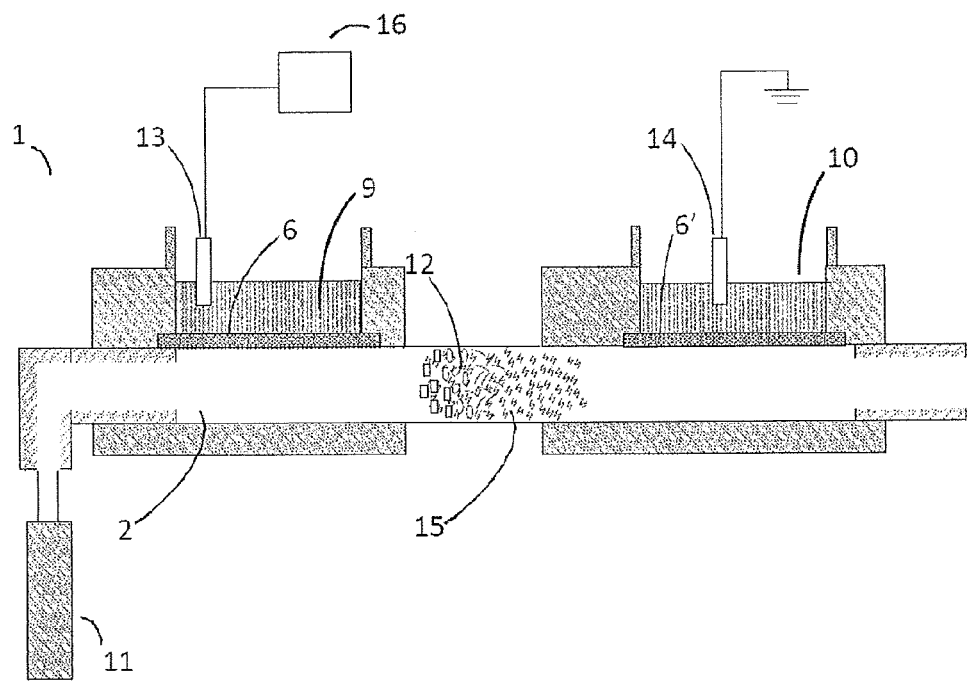
Figure 19C:
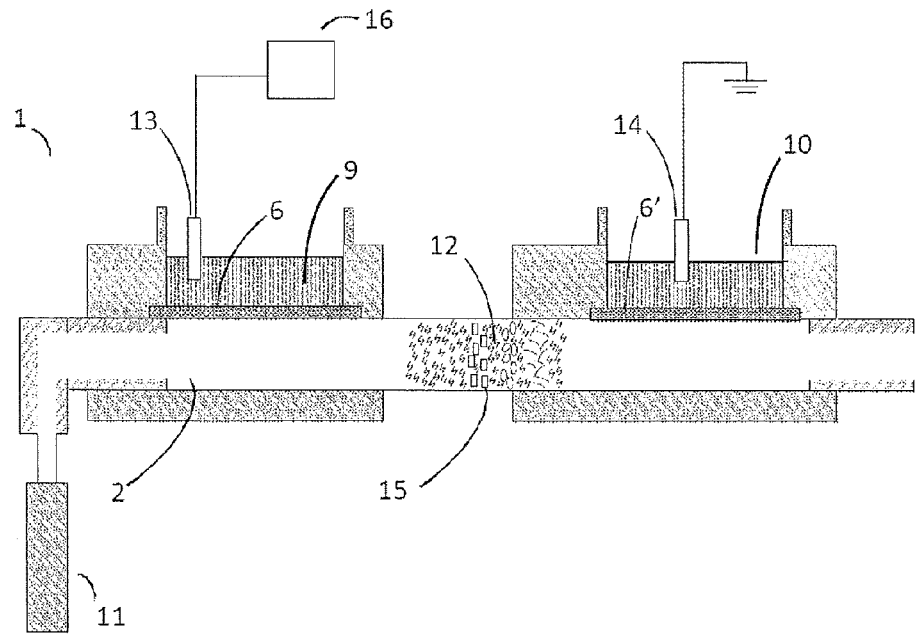
Figure 19D:
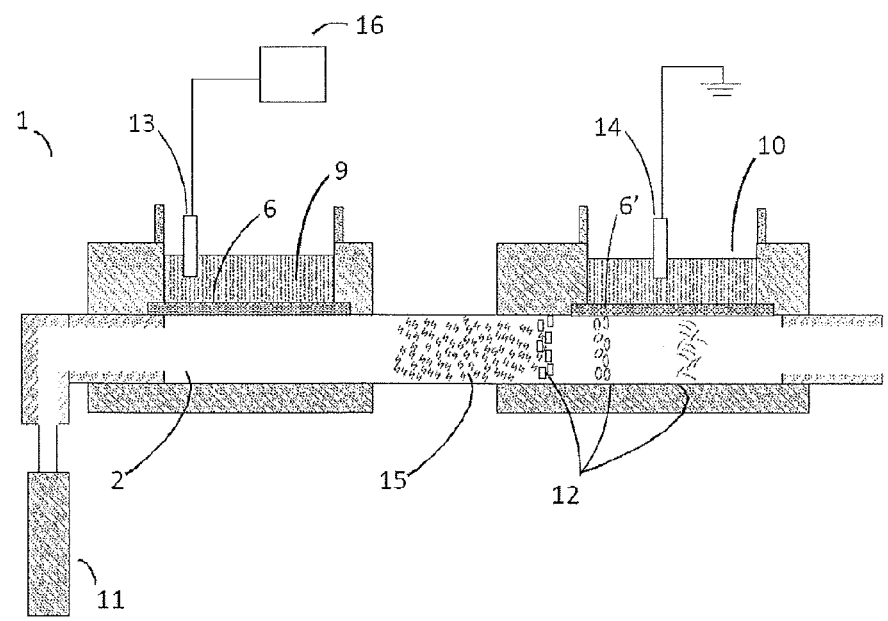

FIG. 19A-D is a schematic representation of a microfluidic electrocapture device under operation. The electrocapture device 1 comprises the sample channel 2 which contains two semipermeable membrane 6 and 6' that separates the sample channel 2 from the electrodes 13 and 14. The pump 11 delivers a constant flow into the sample channel 2. The power supply 16 together with electrodes 13 and 14 deliver an electric field inside the sample channel 2 which capture the charged molecules of interest 15. The analytes of interests 12 are brought in contact with the captured molecules of interest 15, and by this means, the analytes of interest are separated from each other as seen in the consecutives FIGS. 19B, 19C and 19D. The FIG. 19D shows the complete separation of the analytes of interest. The separation is based on the different binding affinities of the analytes of interest to the captured charged molecules.

DETAILED DESCRIPTION OF THE INVENTION

I. Electrospray ionization produces charged droplet using spray devices utilizing unassisted Electrospray or pneumatic nebulization. Unassisted Electrospray requires the formation of a stable Taylor cone jet from the sample solution exiting a channel or tube in the presence of an electric field. Depending on the sample composition, it may not be possible to form a stable Taylor cone at atmospheric pressure (e.g. high conductivity, high surface tension, and high flow rate). In order to solve these limitations, ultrasonic and pneumatic nebulization charged droplet sprayer devices have been developed. Both nebulization techniques can be used in the embodiments described below. Pneumatic nebulization sprayer devices are most widely used for the generation of charged liquid droplets from sample solutions. Pneumatic nebulization produces charged droplets from channels or tube tips in the presence of an electric field by pneumatically shearing the solution as it exits the tube. The gas shearing force acting on the exiting liquid stream is sufficient to create charged droplet sprays even for higher surface tension and higher conductivity solutions and for higher liquid flow rate operating conditions. Charged droplet production using Electrospray (unassisted Electrospray) or pneumatic nebulization in the presence of an electric field (Electrospray with pneumatic nebulization assist) can be used in combination with the present invention.

Electrospray using pneumatic nebulization is the choice when working with flow rates higher than 1 µL/min or with solutions having a chemical composition that are not compatible with unassisted electrospray. Since in the present invention sample analysis need to be performed as fast as possible, Electrospray using pneumatic nebulization is the method of choice when using standard liquid chromatography equipment. Unassisted Electrospray is the method of choice when the present invention is incorporated into microfluidic devices (e.g. chip technologies). Microfluidic devices specially designed for this invention are particularly useful since the smaller volume that this devices have will produce faster results which will reduce back exchange of the deuteration reaction.

The invention includes apparatus and methods to perform hydrogen/deuterium exchange to the analytes of interest. The method is particularly useful, although not restricted, to study proteins or peptides and their interaction with ions, small molecules (e.g. drug candidates), as well as structural changes and/or interactions upon binding to other proteins or peptides and/or ions and/or small molecules.

Figure 1:
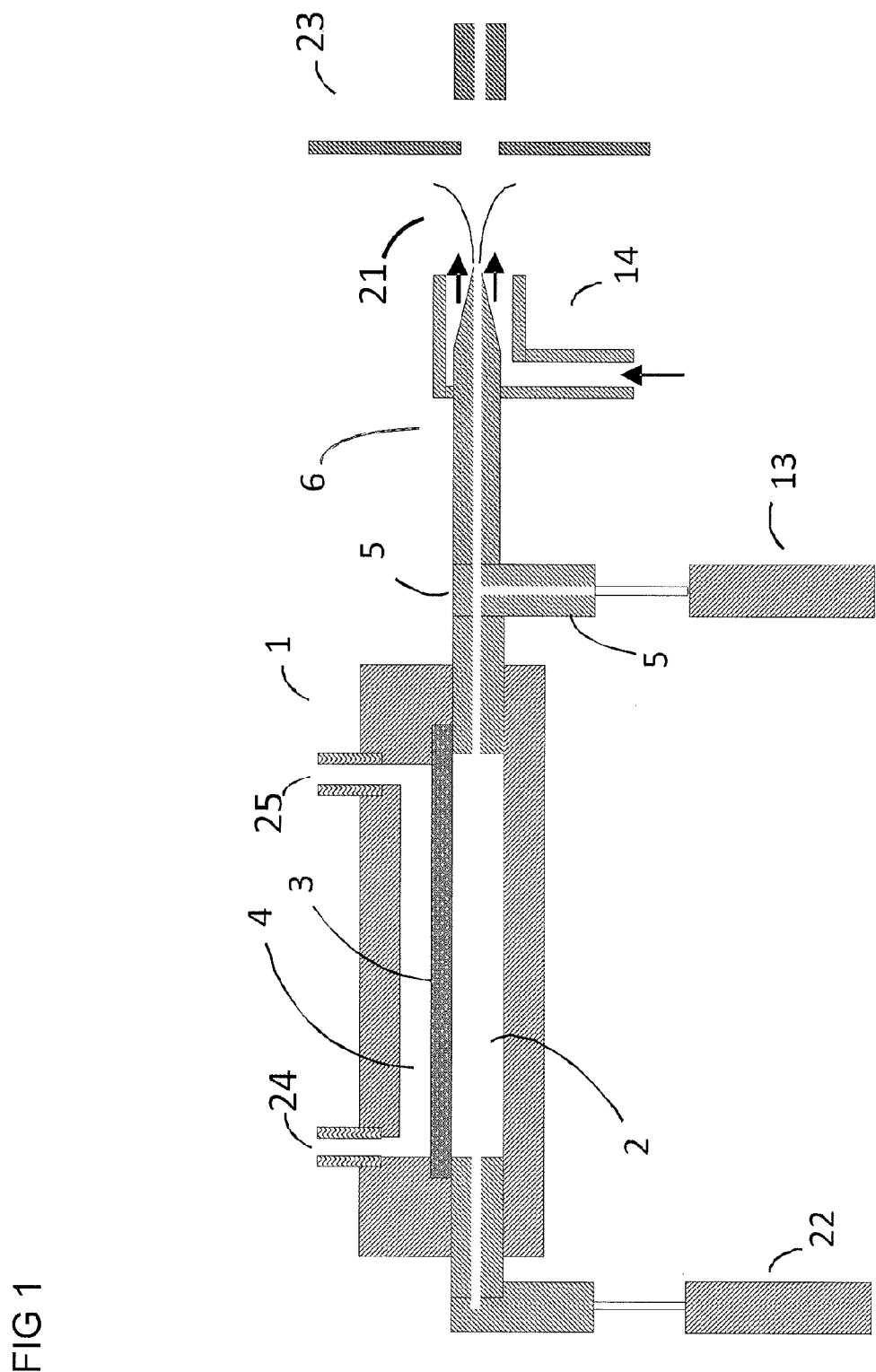
FIG. 1 is a cross section view of the deuteration cell connected to online acidification and online electrospray mass spectrometry with pneumatic nebulization. The deuteration cell 1 comprises two channels (channels 2 and 4), separated by the semipermeable membrane 3. The sample channel 2 comprises the flow carrying the analyte of interest (delivered by pump 22), and it is separated by a semipermeable membrane 3 from the second channel 4 comprising a water solution or deuterium oxide or another deuterated solvent. The solutions in the second channel 4 can be introduced via the inlet 24. The outlet of the second channel 4 is labeled with the number 25. The outlet of the sample channel 2 is connected to a tee channel configuration system 5 (or a tee-connector) in which the sample is acidified, by mixing the sample solution with an acidified solution. The outlet of the tee channel configuration system can be connected to a single exit tip charged droplet sprayer assembly with pneumatic nebulization 6. After electrospray, 21, the ionized sample can enter into the mass spectrometer 23.

One embodiment of the invention comprises at least two channels separated by a semipermeable membrane. One channel contains a flow carrying the analyte of interest, and the second channel has a solution comprising deuterium oxide or another deuterated solvent. Under this configuration, molecules from the deuterated solvent (situated into in the second solution) are able to cross the semipermeable membrane into the flow path containing the sample. As the analyte of interest passes by the section of the flow path having the semipermeable membrane, molecules from the deuterium oxide (or another deuterated solvent) that has passed through the membrane will interact with the analyte of interest, thus promoting the hydrogen-deuterium exchange of the exchangeable hydrogen present in the molecule of interest. The flow of the deuterium oxide might be injected into the cell in manner that it has a different (opposite) direction than the flow carrying the analytes of interest or might be injected into the cell in manner that it has the same direction than the flow carrying the analytes of interest. In this context inlet 24 and outlet 25 might be swapped (e.g. in FIGS. 1 and 2). The direction and magnitude (rate) of the flow might be controlled in order to maximize the performance for a given application.

Semipermeable Membrane

The semipermeable membranes can correspond to a dialysis membrane or filtration membrane or ultrafiltration membrane or ion-selective membrane with a cut-off lower than the analytes of interest. These membranes have a pore size that allows the passage of molecules or atoms smaller than the diameter of the pores. Species with a higher diameter than the pores are hindered from the passage through the membrane. In the case of the present invention, the membrane should allow the passage of water and deuterium oxide but should not allow the passage of the analyte of interest. Since in most of the cases the analyte of interest is a polypeptide, the diffusion of the analyte of interest from the sample channel to the deuterated solvent channel should be greatly reduced and avoided by choosing the right pore size of the membrane. As a general reference, the pores should be not greater than 2 nanometers, since this is the size of a small polypeptide. A better description of the characteristics of the membrane permeability used in the present invention is related to the "membrane cut-off" (this term is well known in the art of membrane science). Membrane cut-off refers to the upper molecular weight limit at which the membrane is permeable to a given analyte. The term can be called as molecular weight cut off. For example, a 3000 daltons cut-off membrane will not allow the passage of molecules with molecular weights higher than 3000 daltons. On the other hand a 3000 daltons cut-off membrane will allow the passage of molecules with molecular weights lower than 3000 daltons. Membranes with a molecular weight cut off of 200 Da might be used for applications involving small molecules.

Ion selective membranes have the characteristic of having small (and charged) pore size holes in which ions of a certain polarity (positively charged ions for cation-selective membranes and negatively charged ions for anion-selective membranes) can easily move from one side of the membrane to the other (high permeability). Ions with different polarity (negatively charged ions for cation-selective membranes and positively charged ions for anion-selective membranes) have a much lower permeability through the membrane. These characteristics are the result of the presence of small and charged pores in the membrane (cation-selective membranes are negatively charged and anion-selective membranes are positively charged), that by charge-repulsion limits the passage of ions having the same polarity than the membrane. Now, since neutral species are not subjected to charge-repulsion (and if they are sufficiently small to pass through the pores) they can freely move from one side to the other. This is the case for water and deuterium oxide, which can easily diffuse from the deuterated solvent channel towards the sample channel. Since in most of the cases the analyte of interest is a polypeptide, the diffusion of the analyte of interest from the sample channel to the deuterated solvent channel will be greatly reduced, thus reducing sample lost. Examples (not limited examples) of cation selective membranes are: polymeric substrate comprising/containing sulphonic and/or carboxylic and/or phosphoric and/or (meth)acrylic acid and/or maleic acid and/or fumaric acid and/or itaconic acid and/or crotonic acid and/or styrene sulfonic acid and/or (meth)acryloyloxypropylsulfonic acid and/or 2-sulfoethyl(meth)acrylate and/or 2-(meth) acryloylamino-2-methyl-1-propanesulfonic acid and/or 2-(meth)acryloylamino-2-propanesulfonic acid and/or vinylsulfonic acid groups. Examples (not limited examples) of anion selective membranes are primary to tertiary amino groups, quaternary ammonium groups and/or pyridinium groups as 4-vinylpyridine and 2-vinylpyridine, and quaternized derivatives thereof; and cationic monomers such as dimethylaminoethyl (meth)acryl, diethylaminoethyl (meth) acrylate, 4-vinylbenzyldimethylamine and 2-hydroxy-3-(meth)acryloxypropyldimethylamine, and salts thereof. The polymeric substrate might comprise aromatic polyether ether ketones, cellulose ester, regenerated cellulose, polysulfone, polyethersulfone, polyvinylidene difluoride, polypropylene, polytetrafluoroethylene, fluorinated ethylene-propylene, nylon, polycarbonate, poly(ether ether ketone) polymers.

Other examples of the semipermeable membrane 3 materials related to the invention may be (not limited examples) sulfonated fluorethylene polymers (like tetrafluoroethylene-perfluoro-3,6-dioxa-4-methyl-7-octenesulfonic acid copolymer which is produced by DuPont with the name of NAFION), sulfonated aromatic polyether ether ketones, cellulose ester, regenerated cellulose, polysulfone, polyethersulfone, polyvinylidene difluoride, polypropylene, polytetrafluoroethylene, fluorinated ethylene-propylene, nylon, polycarbonate, poly(ether ether ketone). The semipermeable membrane 3 material related to the invention can also be comprised of two or more of the material enlisted above as for example (not limited example) a membrane comprised of polyethersulfone and polypropylene. The membrane might also be comprised of composite materials, as for example (not limited example) the materials described above plus carbon fibers and/or glass fibers and/or titanium oxide (e.g. carbon fiber reinforced polytetrafluoroethylene membranes). Specific membranes can be used to maximize the performance for a given application.

The semipermeable membranes 3 utilized in the present invention may be incorporated into the hydrogen/deuterium exchange cell in the form of sheets and/or constructed in the sample channel 2 and/or in the second channel 4 by means of technologies well known the art in the fabrication of microfluidic devices. For example (not limited example) a heated liquid that solidifies at room temperature could be added to imprinted microchannels in a polymer substrate in a manner that covers the channel. After the solidification of the liquid, a monomer solution is placed over the protected channels and polymerized to form a rigid semipermeable copolymer. After, the protective layer is melted and removed, leaving an open microchannel interfaced with a polymer membrane (*Anal. Chem.*, 2006, 78 (8), pp 2565-2570). Another not limited example is explained in Anal Chem. 2007 Aug. 15; 79(16): 6249-6254.

The semipermeable membranes 3 utilized in the present invention comprise membranes with thickness between 1 micrometer and 1000 micrometer. Specific thickness can be used to maximize the performance for a given application (e.g permeability (improve of decreased the permeability of deuterium oxide and/or analyte of interest) and/or robustness and/or resistance to back-pressure).

Hydrogen/Deuterium Exchange Cell

The substrate material of the hydrogen/deuterium exchange cell could be comprised of polycarbonate and/or poly(methyl methacrylate) and/or poly(dimethylsiloxane) and/or polyaryletherketones (like PEEK) and/or glass and/or polyimide in which the channel and/or the semipermeable membrane could be manufactured by UV lithography and/or excimer-laser micro machining, mechanical micro machining (e.g. high-speed cutting, micro milling and electro discharge machining), silicon-microprocessing by dry etching methods, electron beam lithography in silicon wafers and X-ray lithography.

The hydrogen/deuterium exchange cell can also be build using different configurations, as using semipermeable membrane in sheets or tubular membranes and using channels in tubes or flat surfaces.

The hydrogen/deuterium exchange cell might be in a temperature controlled chamber in order to control the velocity (and reproducibility) of the hydrogen/deuterium exchange reaction. Temperatures between 20 and 50 Celsius can be used to increase the reaction rate. Temperature between 0 and 19 Celsius might be used to decrease the reaction rate. Specific temperatures can be used to maximize the performance for a given application.

Further Embodiments

1. Embodiment related to constant infusion of analyte, online deuteration/acidification and ESI-MS. In one embodiment of the invention, the analytes of interest (dissolved in an aqueous solution) can be loaded into a pump 22, which can then be connected to the membrane-based deuterator device 1, seen in FIG. 1. The outlet of the deuterator device can be connected to a Tee-connector 5 in which the sample can be acidified, by mixing the sample solution with an acidified solution (e.g. 0.1% v/v trifluoroacetic acid) delivered by pump 13. The outlet of the tee-connector can be connected to electrospray ionization mass spectrometry which monitors the mass of the analyte of interest over the time. The acidification not only decreases back-exchange but also enhances the signal on the mass spectrometer. In an initial phase, the deuterator device can have water in the second solution. After obtaining the mass of the undeuterated analyte of interest (or one or more analytes of interest), the deuteration procedure can be initiated by changing the composition of the second solution in the membrane-based deuterator device to the deuterated solvent (e.g. deuterium oxide). Since the flow rate of the syringe pump influences the incubation time of the deuteration reaction, different incubation times for the hydrogen/deuterium exchange reaction can be use monitored by increasing or decreasing the syringe pump flow rate. This system can be used to monitor changes in the overall deuteration level of polypeptides (global exchange) upon the binding of ions, small molecules, polypeptides, DNA and sugars to the analytes of interest or after different chemical modifications as oxidations, reductions, methylation, acetylation, farnesylation, biotinylation, stearoylation, formylation, myristoylation, palmitoylation, geranylgeranylation, phosphorylation, sulphation and/or the incorporation of pentoses (hexosamines and/or N-acetylhexosamines) and/or deoxyhexoses (hexoses and/or sialic acid).

2. Embodiment related to constant infusion of analyte, online deuteration/acidification, pepsin column and ESI-MS. In another embodiment of the invention, FIG. 2, the analytes of interest (dissolved in an aqueous solution) can be loaded into a pump 22, which can then be connected to the membrane-based deuterator device 1, wherein the outlet of the deuterator device can be connected to the Tee-connector 5 in which the sample can be acidified, by mixing the sample solution with an acidified solution (e.g. 0.1% v/v trifluoroacetic acid) which can be delivered by pump 13. The outlet of the tee-connector can be connected to the pepsin column 7 that digests the analyte of interest. The pepsin digestion allows a detail picture of what parts of the structure of the analyte of interest have undergone changes in the deuteration characteristics. The outlet of the pepsin column can be connected to electrospray ionization mass spectrometry which monitors the mass of the analyte of interest over the time. The acidification not only decreases back-exchange but also enhances the signal on the mass spectrometer. In an initial phase, the deuterator device can have water in the second solution. After obtaining the mass of the undeuterated analyte of interest (or one or more analytes of interest), the deuteration procedure can be initiated by changing the composition of the second solution in the membrane-based deuterator device to the deuterated solvent (e.g. deuterium oxide). Since the flow rate of the syringe pump influences the incubation time of the deuteration reaction, different incubation times for the hydrogen/deuterium exchange reaction can be monitored by increasing or decreasing the syringe pump flow rate. This system can be used to monitor changes in the overall deuteration level of polypeptides (global exchange) upon the binding of ions, small molecules, polypeptides, DNA and sugars to the analytes of interest or after different chemical modifications as oxidations, reductions, methylation, acetylation, farnesylation, biotinylation, stearoylation, formylation, myristoylation, palmitoylation, geranylgeranylation, phosphorylation, sulphation and/or the incorporation of pentoses (hexosamines and/or N-acetylhexosamines) and/or deoxyhexoses (hexoses and/or sialic acid).

Figure 3:
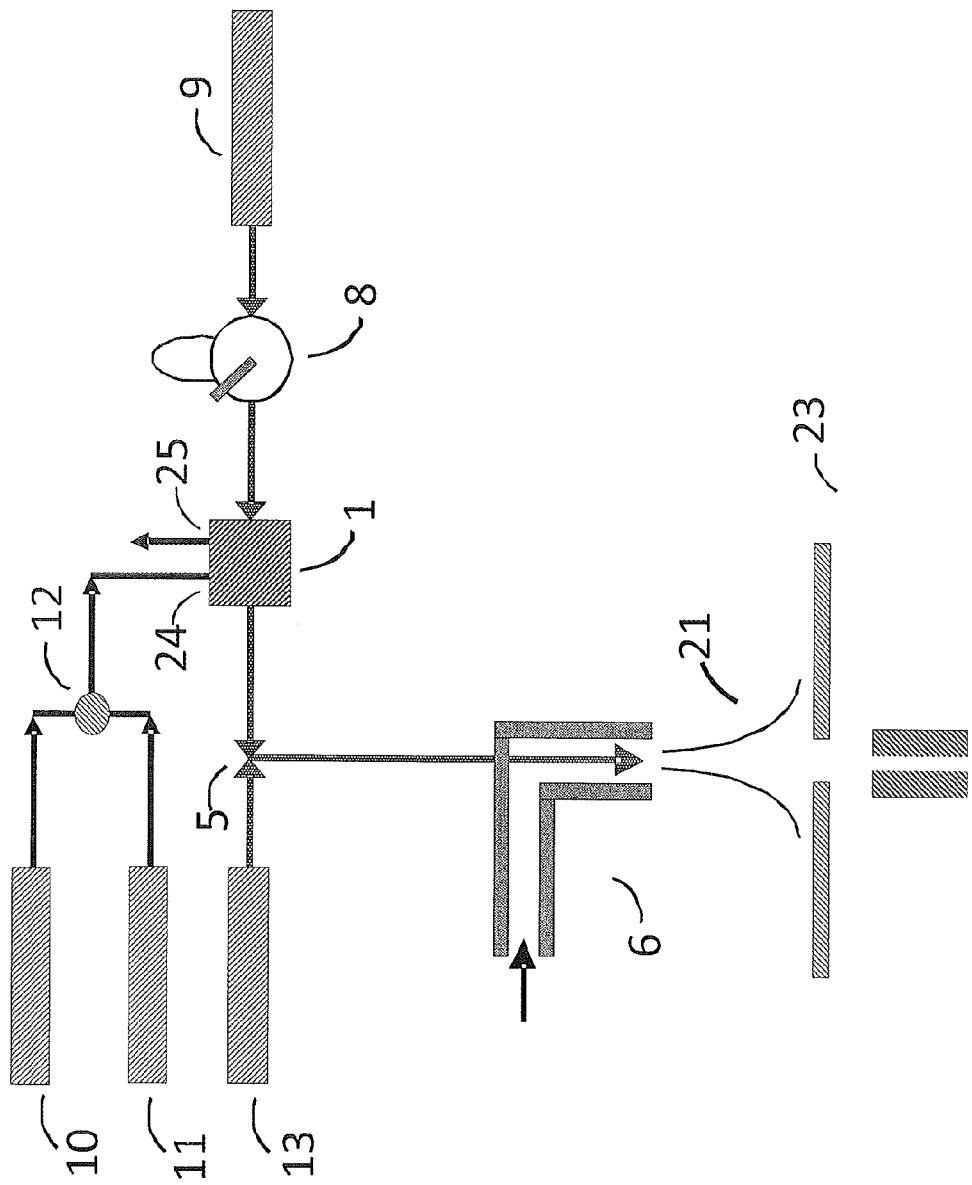
FIG. 3. is a diagram of the deuteration cell coupled to sample injector, acidification and online electrospray mass spectrometry with pneumatic nebulization. The injector 8 (e.g. 6-port injector with a sample loop) is connected to the membrane-based deuterator device 1. The pump 9 (syringe pump or an HPLC pump) is connected to the injector 8 in such a manner that allows the injection of discrete amount of sample (comprising the analytes of interest) into the flow stream. The flow stream carries the sample into the sample channel in the deuterator device 1, where the hydrogen/deuterium exchange reaction takes place. Pumps 10 and 11 deliver deuterated or undeuterated solutions (or a mixture of both) into the second channel in the deuterator device. The inlet of the second channel is labeled with number 24 and the exit with number 25. The outlet of the sample channel in deuterator device 1 is connected to the Tee-connector 5 in which the sample is acidified, by mixing the sample solution with an acidified solution (e.g. 0.1% v/v trifluoroacetic acid) which is delivered by pump 13. The outlet of the tee-connector 5 is connected to electrospray ionization mass spectrometry which monitors the mass of the analyte of interest over the time. The acidification not only decreases back-exchange but also enhances the signal on the mass spectrometer.

3. Embodiment related to sample injector, online deuteration, acidification and ESI-MS. In another embodiment of the invention, shown in FIG. 3, the injector 8 (e.g. 6-port injector with a sample loop) can be connected to the membrane-based deuterator device 1. The pump 9 (syringe pump or an HPLC pump) can be connected to the injector 8 in a manner that allows the injection of discrete amount of sample (containing the analytes of interest) into the flow stream. The flow stream carries the sample into the deuterator device 1, where the hydrogen/deuterium exchange reaction can take place. The outlet of the deuterator device can be connected to the Tee-connector 5 in which the sample is acidified, by mixing the sample solution with an acidified solution (e.g. 0.1% v/v trifluoroacetic acid) which can be delivered by pump 13. The outlet of the tee-connector 5 can be connected to electrospray ionization mass spectrometry which monitors the mass of the analyte of interest over the time. The acidification not only decreases back-exchange but also enhances the signal on the mass spectrometer. In an initial phase, the deuterator device has water in the second solution. After obtaining the mass of the undeuterated analyte of interest (or one or more analytes of interest), the deuteration procedure can be initiated by changing the composition of the second solution in the membrane-based deuterator device to the deuterated solvent (e.g. deuterium oxide). Since the flow rate of the syringe pump influences the incubation time of the deuteration reaction, different incubation times for the hydrogen/deuterium exchange reaction can be monitored by increasing or decreasing the syringe pump flow rate. This system can be used to monitor changes in the overall deuteration level of polypeptides (global exchange) upon the binding of ions, small molecules, polypeptides, DNA and sugars to the analytes of interest or after different chemical modifications as oxidations, reductions, methylation, acetylation, farnesylation, biotinylation, stearoylation, formylation, myristoylation, palmitoylation, geranylgeranylation, phosphorylation, sulphation and/or the incorporation of pentoses (hexosamines and/or N-acetylhexosamines) and/or deoxyhexoses (hexoses and/or sialic acid).

4. Embodiment related to sample injector, online deuteration, acidification, short chromatography column and ESI-MS. In another embodiment of the invention, shown in FIG. 4A, the injector 8 (e.g. 6-port injector with a sample loop) can be connected to the membrane-based deuterator device 1, the pump 9 (syringe pump or an HPLC pump) can be connected to the injector 8 in such a manner that allows the injection of discrete amount of sample (containing the analytes of interest) into the flow stream. The flow stream carries the sample into the deuterator device 1, where the hydrogen/deuterium exchange reaction can take place. The outlet of the deuterator device can be connected to the tee-connector 5 in which the sample can be acidified, by mixing the sample solution with an acidified solution (e.g. 0.1% v/v trifluoroacetic acid) which can be infused by pump 13. The acidification not only decreases back-exchange but also enhances the signal on the mass spectrometer. The outlet of the tee-connector 5 can be connected to the valve 14 (e.g. 6-port valve) in such a manner that allows the injection of discrete amounts of acidified sample into the chromatography column 16 (e.g. reverse-phase chromatography, either C-18 or C8). The outlet of the chromatography column 16 can be connected to an online electrospray mass spectrometer with pneumatic nebulization 6. In another configuration, the outlet port from the valve 14 can be connected to another valve, e.g. a six port valve or a ten port valve. The configuration using another six port valve (valve 16) is shown in FIG. 4B. An advantage of using the configuration shown in FIG. 4B, is that unwanted compounds that are separated by the short chromatography column 16 can be diverted to waste instead of being directed towards the mass spectrometer. Once the sample has been cleaned, the valve 16 can be switched to deliver the analyte of interest to the mass spectrometer.

In order to reduce back exchange, the valve and chromatography column can be placed into a cold chamber (e.g. under an ice-bath or a peltier-cooled chamber or a modified refrigerator or freezer). The outlet of the chromatography column can be connected to an electropspray ionization mass spectrometer which monitors the mass of the analyte of interest over the time. Using this embodiment, samples can be injected via the first injection valve, deuterated using the membrane-based deuterator device, concentrated and/or cleaned and/or separated using the chromatography column and analyzed by electrospray mass spectrometry. After obtaining the mass of the undeuterated analyte of interest (or one or more analytes of interest), the deuteration procedure can be initiated by changing the composition of the second solution in the membrane-based deuterator device to the deuterated solvent (e.g. deuterium oxide). Since the flow rate of the syringe pump influences the incubation time of the deuteration reaction, different incubation times for the hydrogen/deuterium exchange reaction can be monitored by increasing or decreasing the syringe pump flow rate. This system can be used to monitor changes in the overall deuteration level of polypeptides (global exchange) upon the binding of ions, small molecules, polypeptides, DNA and sugars to the analytes of interest or after different chemical modifications as oxidations, reductions, methylation, acetylation, farnesylation, biotinylation, stearoylation, formylation, myristoylation, palmitoylation, geranylgeranylation, phosphorylation, sulphation and/or the incorporation of pentoses (hexosamines and/or N-acetylhexosamines) and/or deoxyhexoses (hexoses and/or sialic acid).

5. Embodiment related to sample injector, online deuteration, acidification, pepsin column and ESI-MS. In another embodiment of the invention, shown in FIG. 5A, the injector 8 (e.g. 6-port injector with a sample loop) can be connected to the deuterator device 1, and the pump 9 (syringe pump or an HPLC pump) can be connected to the injector 8 in such a manner that allows the injection of discrete amount of sample (comprising the analytes of interest) into the flow stream. The flow stream carries the sample into the deuterator device 1, where the hydrogen/deuterium exchange reaction takes place. The outlet of the deuterator device can be connected to the tee-connector 5 in which the sample is acidified, by mixing the sample solution with an acidified solution (e.g. 0.1% v/v trifluoroacetic acid), which can be delivered by pump 13. The acidification not only decreases back-exchange but also enhances the signal on the mass spectrometer. The outlet of the tee-connector 5 can be connected to the pepsin column 7 that digests the analyte of interest. The pepsin digestion allows a detail picture of what parts of the structure of the analyte of interest have undergone changes in the deuteration characteristics. The out let of the pepsin column 7 can be connected to an online electrospray mass spectrometer with pneumatic nebulization 6. In another embodiment, shown in FIG. 5B, the pepsin column 7 can be connected to the valve 14 (e.g. 6-port valve) in such a manner that allows the injection of discrete amounts of the digested sample into the online electrospray mass spectrometer with pneumatic nebulization 6.

6. Embodiment related to sample injector, online deuteration, acidification, pepsin column, short chromatography column and ESI-MS. In another embodiment of the invention, shown in FIG. 6A, the injector 8 (e.g. 6-port injector with a sample loop) can be connected to the deuterator device 1, and the pump 9 (syringe pump or an HPLC pump) can be connected to the injector 8 in such a manner that allows the injection of discrete amount of sample (comprising the analytes of interest) into the flow stream. The flow stream carries the sample into the deuterator device 1, where the hydrogen/deuterium exchange reaction takes place. The outlet of the deuterator device 1 can be connected to the tee-connector 5 in which the sample can be acidified, by mixing the sample solution with an acidified solution (e.g. 0.1% v/v trifluoroacetic acid), which can be delivered by pump 13. The acidification not only decreases back-exchange but also enhances the signal on the mass spectrometer. The outlet of the tee-connector 5 can be connected to the pepsin column 7 that digests the analyte of interest. The pepsin digestion allows a detail picture of what parts of the structure of the analyte of interest have undergone changes in the deuteration characteristics. The outlet of the pepsin column 7 can be connected to the six port valve 14 in a manner that the sample coming from the pepsin column 7 fills the loop from the valve 14. Additionally, the valve 14 can be configured with the short chromatographic column 16 (e.g. C-18 or C-4) in a manner that the valve 14 allows discrete amounts of sample (loaded in the loop) into the short chromatographic column 16. The outlet of the short chromatographic column 16 can be connected to the online electrospray mass spectrometer with pneumatic nebulization 6.

In another configuration, shown in FIG. 6B, the valve 14 can be connected to the short chromatographic column 16 by a six port valve (as seen in FIG. 6B) or by using a ten port valve (as seen in FIG. 6C).

7. Embodiment related to sample injector, online deuteration, acidification, pepsin column, short chromatography column, analytical column and ESI-MS. In another embodiment of the invention, shown in FIG. 7A and FIG. 7B, the injector 8 (e.g. 6-port injector with a sample loop) can be connected to the deuterator device 1, and the pump 9 (syringe pump or an HPLC pump) can be connected to the injector 8 in such a manner that allows the injection of discrete amount of sample (comprising the analytes of interest) into the flow stream. The flow stream carries the sample into the deuterator device 1, where the hydrogen/deuterium exchange reaction takes place. The outlet of the deuterator device 1 can be connected to the tee-connector 5 in which the sample can be acidified, by mixing the sample solution with an acidified solution (e.g. 0.1% v/v trifluoroacetic acid), which can be delivered by pump 13. The acidification not only decreases back-exchange but also enhances the signal on the mass spectrometer. The outlet of the tee-connector 5 can be connected to the pepsin column 7 that digests the analyte of interest. The pepsin digestion allows a detail picture of what parts of the structure of the analyte of interest have undergone changes in the deuteration characteristics. The outlet of the pepsin column 7 can be connected to the six port valve 14 can be configured in such a manner (as depicted on FIG. 7A) that the sample coming from the pepsin column 7 fills the loop from the valve 14. The six port valve 14 can be connected to the ten port valve 17 in such a manner (as depicted in FIG. 7A) that allows the injection of discrete amounts of the analyte of interest (analytes of interest loaded into the sample loop at the valve 14) into the short chromotographic column 16, as seen in FIG. 7B. The chromotographic column 16, provides concentration and removal of unwanted compounds from the sample solution. Once said analytes are concentrated and cleaned, the valve 17 send the analytes of interest to the analytical column 18 (e.g. C-8 or C-18) which can be online connected to the electrospray mass spectrometer with pneumatic nebulization 6, as shown in FIG. 7B.

This configuration allows an efficient coupling of the pepsin column to two chromatographic columns, one short pre-column (C-8 or C-18) for concentration and/or desalting step, and another column, that serves as an analytical column to perform an efficient separation. In order to reduce back exchange, the valve and chromatography columns can be placed into a cold chamber (e.g. under an ice-bath or a peltier-cooled chamber or a modified refrigerator or freezer). The outlet of the chromatography column can be connected to an electropsray ionization mass spectrometer which monitors the mass of the analyte of interest over the time. Using this embodiment, samples can be injected via the first injection valve, deuterated using the membrane-based deuterator device, concentrated and/or cleaned and/or separated using the chromatography column and analyzed by electrospray mass spectrometry. After obtaining the mass of the undeuterated analyte of interest (or one or more analytes of interest), the deuteration procedure can be initiated by changing the composition of the second solution in the membrane-based deuterator device to the deuterated solvent (e.g. deuterium oxide). Since the flow rate of the syringe pump influences the incubation time of the deuteration reaction, different incubation times for the hydrogen/deuterium exchange reaction can be use monitored by increasing or decreasing the syringe pump flow rate. This system can be used to monitor changes in the overall deuteration level of polypeptides (global exchange) upon the binding of ions, small molecules, polypeptides, DNA and sugars to the analytes of interest or after different chemical modifications as oxidations, reductions, methylation, acetylation, farnesylation, biotinylation, stearoylation, formylation, myristoylation, palmitoylation, geranylgeranylation, phosphorylation, sulphation and/or the incorporation of pentoses (hexosamines and/or N-acetylhexosamines) and/or deoxyhexoses (hexoses and/or sialic acid).

8. Embodiment related to sample injector, online deuteration, acidification, short chromatography column, analytical column and ESI-MS. An injector 8 can be connected to the deuteration cell 1. Pump 9 can be connected to the injector 8 in a manner that allows the injection of discrete amount of sample (comprising the analytes of interest) into the deuteration cell 1, where the hydrogen/deuterium exchange reaction can be performed. The solution infused into the second channel in the deuteration cell can be pumped by the pumps 10 and/or 11, which can be connected to the inlet of the second channel 4 by the tee-connector 12. The outlet of the deuterator device 1 can be connected to a tee channel configuration system 5 (or a tee-connector) in which the sample is acidified, by mixing the sample solution with an acidified solution pumped into the tee-connector 5 by the pump 13. The outlet of the tee channel configuration system 5 can be connected to the six-port valve 14 which allows the injection of discrete amount of the analyte of interest into the ten-port valve 17 comprising the short chromatography column 16 and the analytical column 18. The configuration using one six-port valve and one ten-port valve allows an efficient coupling to two chromatographic columns, one short precolumn (C-8 or C-18) for concentration and/or desalting step, and another column, that serves as an analytical column to perform an efficient separation. This particular embodiment is useful in applications where there is no need for pepsin digestion, but it is necessary to carry out desalting and/or separation and/or concentration.

9. Embodiment related to different ionization techniques and mass spectrometers. All the embodiments described above can be used utilizing unassisted electrospray ionization, using nanoflow electrospray ion sources or picoflow electrospray ion sources by using picotips, nanotips and other related interfaces and/or devices and/or hardware. In addition, all the embodiments above can be used in mass spectrometers with grounded sources or ungrounded sources.

10. Embodiment related to different ionization techniques. All the embodiments described above can be used in mass spectrometers having matrix-assisted laser desorption ionization mass spectrometry (MALDI-MS) and/or inductively coupled plasma (ICP-MS) and/or field desorption or field ionization (FD/FI) and/or liquid injection FD ionization and/or fast atom bombardment and/or thermo spray and/or desorption/ionization on silicon (DIOS) and/or Direct Analysis in Real Time (DART) and/or atmospheric pressure chemical ionization (APCI) and/or secondary ion mass spectrometry (SIMS) and/or spark ionization and/or thermal ionization (TIMS) and/or Ion Attachment Ionization Desorption Electrospray Ionization (DESI) and/or ElectroSonic Spray Ionization (ESSI) and/or Atmospheric Pressure Chemical Ionization (APCI) including desorption APCI and/or Field-Free Desorption APCI ionization techniques.

11. Embodiment related to ElectroCapture described in WO/2004/056697 entitled Method and device for capturing charged molecules traveling in a flow stream. In brief, the electrocapture system utilizes two sections of ion selective membranes to produce an electric field inside the sample channel by an external electric field applied by electrodes located on the other side of the membrane. An electrocapture system can be coupled with the present invention by locating two (or more) semipermeable membranes and their respective electrodes either after the outlet of the deuteration cell or by locating the deuteration cell between a set of electrocapture membranes (in this case the deuteration cell will be inside the electric field). A non limited example of an electrocapture system coupled to a hydrogen/deuterium exchange cell can be seen in FIG. 10. One advantage of coupling a electrocapture cell with a deuteration cell is that the molecules could be capture in the flow stream meanwhile the hydrogen/deuterium exchange reaction is happening, thus the deuteration time might be increased and/or improved.

12. Embodiment related to controlling system. All the embodiments described comprising valves, pumps above can be controlled using electrical circuits or computers to coordinate and activate and/or optimize the processes explained in the said embodiments.

13. Embodiment related to automation. All the embodiments described above can be combined with an automated injector, as for example a CTC PAL autosampler (autoinjector) in a manner that a automated hydrogen/deuterium exchange platform is constructed to analyze two or more samples in an unattended manner.

14. Embodiment related to sample analysis. The system could be further connected to a software which analyzes and/or displays the result as soon the sample analyzed or during analysis. The software could constantly monitor changes in the deuteration level of the analytes of interest and report or highlight said changes.

15. Embodiment related to the digestion of the analyte of interest. The analyte of interest (e.g. polypeptide) might be digested or cleaved by one or more digestion proteins or reagent as (no limited examples) Arg-C proteinase and/or Asp-N endopeptidase and/or Asp-N endopeptidase+N-terminal Glu and/or BNPS-Skatole and/or Caspase1 and/or Caspase2 and/or Caspase3 and/or Caspase4 and/or Caspase5 and/or Caspase6 and/or Caspase7 and/or Caspase8 and/or Caspase9 and/or Caspase10 and/or Chymotrypsin-high specificity (C-term to [FYW], not before P) and/or Chymotrypsin-low specificity (C-term to [FYWML], not before P) and/or Clostripain (Clostridiopeptidase B) and/or CNBr and/or Enterokinase and/or Factor Xa and/or Formic acid and/or Glutamyl endopeptidase and/or GranzymeB and/or Hydroxylamine and/or Iodosobenzoic acid and/or LysC and/or LysN and/or NTCB (2-nitro-5-thiocyanobenzoic acid) and/or Pepsin and/or Proline-endopeptidase and/or Proteinase K and/or Staphylococcal peptidase I and/or Tobacco etch virus protease and/or Thermolysin and/or Thrombin and/or Trypsin. The enzymes or reargents could be used as a column (packed material) or injected into the flow stream (as liquid).

16. Embodiment related to the fragmentation methods provided by mass spectrometry. In addition to the measurement of the mass over charge ratio by the mass spectrometer, said instrument might provide structural information of the analyte of interest by the use of at least one fragmentation method as, for example (non limited examples) the use of mass spectrometers performing MS/MS by using Collision-induced dissociation (CID) and/or Electron capture dissociation (ECD) and/or Electron transfer dissociation (ETD) and/or infrared multiphoton dissociation (IRMPD) and/or blackbody infrared radiative dissociation (BIRD). The fragmentation methods might be used to investigate which part of the analyte of interest incorporated deuterium (for a given condition of time and/or flow rate and/or temperature and/or in the presence of an interacting analyte). The fragmentation methods could be utilized to perform bottom up (characterize and/or identify proteins by proteolytic digestion of proteins prior to analysis by mass spectrometry) or by using top down (fragmentation of the target protein by ECD or ETD) approaches. Both techniques can map which parts of the structure of the analyte of interest incorporate deuterium, therefore it could be used (in combination with the present invention) to monitor structural changes a molecule of interest and/or study the interaction of a molecule of interest with other molecules or atoms.

Experimental Data

Figure 2:
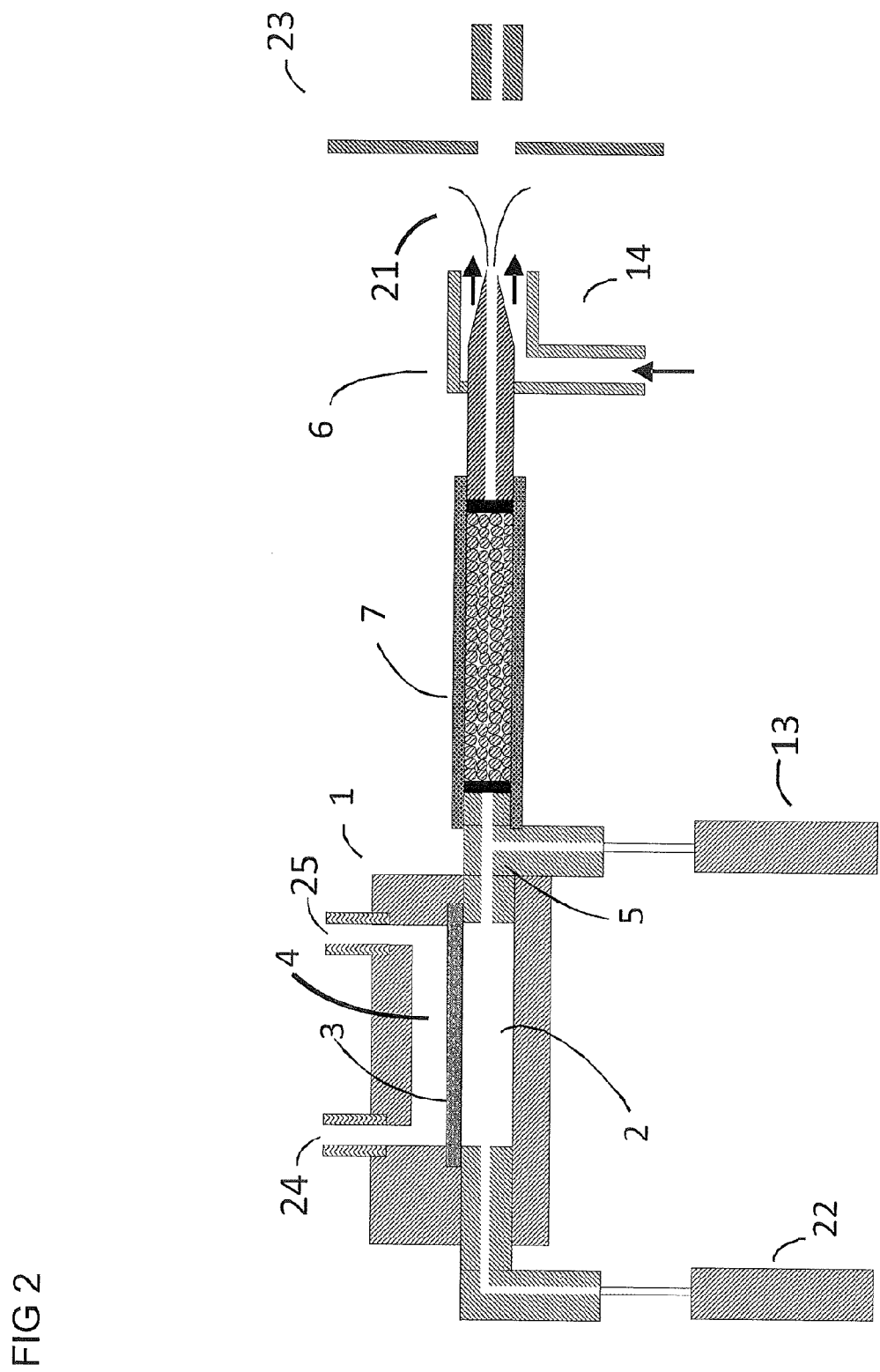
FIG. 2 is a cross section view of the deuteration cell connected to online acidification, online pepsin digestion and online electrospray mass spectrometry with pneumatic nebulization. The deuteration cell 1 comprises two channels (channels 2 and 4), separated by the semipermeable membrane 3. The sample channel 2 comprises the flow carrying the analyte of interest (delivered by pump 22), and it is separated by a semipermeable membrane 3 from the second channel 4 comprising a water solution or deuterium oxide or another deuterated solvent. The solution in the second channel 4 can be introduced via the inlet 24. The outlet of the second channel 4 is labeled with the number 25. The outlet of the deuterator device 1 is connected to tee channel configuration system 5 (or a tee-connector) in which the sample is acidified, by mixing the sample solution with an acidified solution. The outlet of the tee channel configuration system is connected to a pepsin column 7 which then is connected to a single exit tip charged droplet sprayer assembly with pneumatic nebulization 6. After electrospray, 21, the ionized sample can enter into the mass spectrometer 23.

The performance of the present invention was tested by conducting on-line labeling of [Glu1]-Fibrinopeptide B, a 14-residue peptide with no known secondary structure elements. If the HDx cell has the same efficiency as "off-line" deuteration, even rapid flow rates should provide near-complete labeling of the backbone amides. We observed an incorporation of 12.8-13.4 deuterons at flow rates between 1 and 0.4 µL/min, which corresponds to 91.4-95.5% deuteration (FIG. 2 and Table 1). The degree of deuterium incorporation is therefore close to the theoretical deuteration maximum (14 deuterons), This indicates that flow-rate dependent deuterium incorporation changes are not due to low deuteration efficiency, but dependent on exposure times and the individual backbone amide exchange rates. FIG. 11 corresponds to hydrogen/deuterium exchange data produced by the present invention allowing on-line deuteration of [Glu1]-Fibrinopeptide B at different flow rates. The data is compared against off-line deuteration (direct dilution with deuterium oxide).

Advantages of the Present Invention

Comparing the characteristics of the state-of-the art technologies to perform hydrogen/deuterium exchange, several advantages in using this invention are obtained. First, the sample does not need to be volumetrically diluted with the deuterated solvent (deuterium oxide), therefore increasing the sensitivity of the overall methodology. Second, since the hydrogen/deuterium exchange reaction happens in the hydrogen/deuterium exchange cell, the mixing of the analyte of interest with the deuterated solvent occurs online without the necessity of physically transfer (e.g. pipetting) the sample comprising the analyte of interest to the reservoir, tube or vial containing the deuterated solvent, or vice versa. Third, since the deuteration can be produced online meanwhile the sample passes through the hydrogen/deuterium exchange cell, the automation of the overall procedure can easily be obtained by an automated injector setup and at least 3 pumps (in the most simple set up, one pump supplying the hydrodynamic flow for the sample, a second pump for the deuterium oxide and a third pump for the acidification step). Fourth, the present invention does not comprise the use of an electric field or an electric potential across the membrane. This feature makes this invention safer for the end-user (no possibility of electrical shock) and facilitates simplified manufacturing procedures since the cell might be built in plastics or other electrically non-conductive materials. Electrically conductive material might be used in order to control the temperature, or might be used to combine deuterium exchange to electrocapture.

Another advantage of the present invention is that the same device could be used to inject different reagents, compounds, solutions from the deuteration channel to the sample channel. For example (non limited examples), instead of infusing deuterium oxide as reagent, hydrogen peroxide ($H_2O_2$) could be infused into the second solution to promote oxidation of the analytes of interest situated in the sample channel. In this context, other solutions containing carbohydrates, RNA, DNA, drugs, ions and solution with different ionic strength and/or pH could be infused into the second solution in order to investigate the effect upon the molecule of interest located in the sample solution channel.

II. In FIG. 12 a chemical analysation device 1 according to one example of the invention is shown. The chemical analysation device 1 comprises a sample receiver 3 arranged to receive a chemical sample comprising at least one compound to be analysed, a separator 5 arranged to separate different chemical compounds in the sample from each other, a sample dividing member 7 arranged to divide the received and separated chemical sample into at least a first and a second sample parts, and a first 9 and a second 11 detectors arranged to detect and/or to analyse the at least one compound to be analysed in the second sample part. The chemical analysation device 1 further comprises a computer 13 arranged to download a computer program product 15 comprising a computer program. The computer 13 is arranged to execute the program 15, and to exert electronic control of the components in the analysation device 1 based on the program. The computer 13 is also arranged to receive measurement data from the detectors, to combine the measurement data, and to process and analyse the data to acquire desired information, based on instructions in the computer program product 15.

In this example the first 9 and second 11 detectors are mass spectrometers, wherein the chemical analysation device further comprises a first ionizer 17 arranged to ionize the first sample part and to forward the ionized molecules of the first sample part to the first detector 9, and a second ionizer 19 arranged to ionize the second sample part and to forward the ionized molecules of the second sample part to the second detector 11.

The chemical analysation device 1 is in this example arranged to allow a continuous flow of a carrier medium through the device. The sample receiver 3 is arranged to deliver the sample into or onto the carrier medium, wherein the carrier medium conveys the sample within itself for transport through the analysation device. In this example the carrier medium is a gas, but the carrier medium may also be a fluid, a liquid or a solid.

The separator 5 is in this example a chromatograph. Since the carrier medium is a gas, the separator is in this example a gas chromatograph. The gas chromatograph 5 may separate different compounds in the sample from each other to simplify analysis of each compound individually. Thus the results from an analysis of one compound will preferably remain unmixed-up with the results from an analysis of another compound. It may be however that the gas chromatograph 5 is unable to separate two or more compounds from each other completely, or not at all. In this case the detectors 9, 11 are adapted to identify two or more compounds simultaneously.

The sample dividing member 7 comprises an inlet 21 connected with the separator 5 for receiving a continuous flow of a carrier medium having the separated sample carried therein. The sample dividing member is arranged to divide the carrier medium in the form of a gas stream, and thus also the sample, into two outgoing gas streams, and thus into the two sample parts. The sample dividing member 7 also comprises a first 23 and a second 25 outlet for delivering the first and the second sample parts to desired destinations, such as to forward the divided sample parts to the different detectors 9, 11. In this example the dividing member 7 is arranged to further the first sample part to the first detector 9 and the second sample part to the second detector 11.

The sample dividing member 7 is arranged to divide the flow so that each of the first and second sample parts will contain nearly identical proportions of the compounds contained therein. Due to the continuous flow and the previous separation of the sample, the composition and chemical proportions of the received sample will however differ at different points of time in the divider 7. As an example, in case the first sample at a specific instant contains 10% by volume of compound A and 20% by volume of compound B, the remaining part being carrier gas, the second sample part should contain the same proportions within a reasonable tolerance limit at that time.

The sample dividing member 7 further comprises an adjustment member 27 arranged to allow an adjustment of the dividing ratio, in flow, volume or in weight, between the first and the second parts. In this example the adjustment member 27 may divide the carrier and sample flow so that from 10 to 100% by volume of the flow is forwarded to the first detector 9, while simultaneously 0 to 90% by volume of the flow is forwarded to the second detector 11. The adjustment member 27 may be adjusted manually by a user, or electronically by control signals from the computer 13. Preferably, the dividing ratio is adjusted so that the travelling time for the first and second sample parts to reach its respective detector is identical to within reasonable tolerances. This ensures that acquired measurement data from the two detectors 9, 11 may more easily be correlated with each other. The adjustment may be dependent on factors such as the present carrier medium flow, the length and inner diameter of the conductors leading to the first and second detectors, and any differences in sample speed through the conductors, for example due to adherence to the walls of a conductor. Preferably, the two conductors leading between the sample dividing member and the detectors are therefore substantially equal to counter any differences.

The first ionizer 17 is in this example arranged to ionize the at least one compound to be analysed in the first sample part so that at least a majority of the ionized molecules of the compound to be analysed remain intact. In this example the first ionizer is arranged to ionize the compound to be analysed by bringing it in contact with excited, but otherwise inert, molecules having excitation energies higher than or equal to the ionization energy of the compound to be analysed. The excited, inert molecules may be excited by any known methods, such as corona discharge. In one embodiment the first ionizer ionizes the first sample at atmospheric pressure and possibly in the ambient air. Preferably however, the ionization takes place in a vacuum or at least under protection of the carrier medium and possibly in the presence of another protection gas. Examples of ioniziers usable with the invention include, but are not limited to, the ionizers shown in US 2007/0187589, and U.S. Pat. No. 6,949,741. Other types of ionizers include APCI, DART, DAPCI, ff DAPCI, DESI, MALDI and others.

By including a mass spectrometer 9 analysing intact molecules from the sample the total molecular weights of the compounds may be used for identifying the individual chemicals contained in the sample. The resolution of the mass spectrometer 9 is preferably greater than or equal to 5000, and ore preferably greater than or equal to 9000, as measured by the FWHM-method. In this example the resolution of the mass spectrometer is greater than or equal to 10 000. Hence the mass spectrometer 9 also has the resolving power to determine the presence of two different high molecular mass compounds with nearly the same mass. Thus, the first mass spectrometer gives information on the number of different compounds as well as their total weights.

The second ionizer 19 is in this example arranged to ionize the at least one compound to be analysed in the second sample part so that at least a majority of the ionized molecules of the compound to be analysed are fragmented. In this example the ionization of the second sample is effected by contacting the second sample with a spray of electrons. The ionization is preferably carried out under vacuum conditions. Examples of ionizers usable with the invention include, but are not limited to, electron ionization, chemical ionization, electro spray, electron impact, glow discharge, spark ionization, etc. However any future technology for ionization may be used for the first and the second ionizers, respectively.

By including a second mass spectrometer 11 analysing fragments of molecules information on structure, constituents and functional groups within the compound to be analysed is obtained. Many molecules have known fragment distributions, wherein a molecule may sometimes also be identified with the second mass spectrometer. Furthermore, the transfer of molecules from the second ionizer and into the mass spectrometer is nearly at 100%, and the ratio of ionization of molecules is also usually known, wherein the second mass spectrometer may be used to quantify the amount or concentration of a compound within the sample.

The processing unit 13 in the form of a computer 13 is arranged to receive measurement data from the first 9 and second detectors 11. The computer 13 is further arranged to fit the data with information in at least one database comprising libraries with molecules and associated stored measurement values. In this example the computer 13 is then arranged to present one or more suggestions for the identity of the measured compounds departing from the fit between the measured data and the stored data in the libraries, if a molecule in the library fit the data within a confidence interval.

In this example, by including two mass spectrometers utilising different ionization methods for analysation of both intact molecules and their fragments, and from the more certain correlation of the two sets of measurement values with each other, the computer 13 gains more information on different aspects of each compound within the sample, wherein the quality of the analysation may be improved considerably. In that both information on fragments and intact molecules is available the probability of successfully identifying a molecule increases. Further, the resolving power of the analysation may increase and furthermore, it may be possible to narrow down the suggestions from a measurement.

In an example of the narrowing power of the chemical analysation device 1 a sample may contain a compound having a fragment distribution very similar to one or more other compounds. Alternatively, the sample could contain a compound having a molecular weight which is the same as many other compounds. From the information on both the intact molecular weight and the fragment distribution the computer may then determine which of these compounds fits the spectrums from both the detectors.

In an example of the resolving power of the chemical analysation device a sample may contain two compounds having similar fragment distributions. From a fragment spectrum alone the computer would search for one molecule having a fragment distribution in the m/z spectrum being the sum of the two fragment distributions of the two molecules. However, from the information on intact molecular weight of the first detector, and in that the computer 13 know that the information from the first detector most likely is only from intact molecules, the computer realizes that two molecules are present, so that a better fit may be found. Furthermore, the computer 13 may search from only those molecules having the measured total weights.

In that the chemical analysation device also comprises a separator 5 the composition of a sample could also more easily be discerned, so that almost all compounds in a complex sample of several compounds could be identified. In case the separator 5 is unable to separate two compounds in the sample from each other the measurement results on intact molecular weights from the first mass spectrometer may help remedy the problem.

In FIG. 13 yet another example of an analysation device 29 according to one aspect of the invention is shown. The analysation device 29 is similar to the analysation device in FIG. 12, and when the two devices comprise the same components with the same functions the same reference number has been used.

The analysation device comprises a second sample dividing member 31 comprising an inlet 33 connected with the first outlet 23 of the first sample dividing member 7, wherein three outlets 25, 35, 37 from the sample dividing members are achieved. Analogously, yet a third, fourth etc sample diving member could of course be provided if desired. In another example a single sample dividing member could instead be fitted with corresponding three, four or more outlets.

The first 9 and second 11 detectors are in this example connected with the first 35 and second 37 outlets of the second sample dividing member 31. The analysation device 29 further comprises a third detector 39 connected with the second outlet 25 of the first sample dividing member 7. The third detector 39 is in this example a flame ionisation detector, arranged to ionize molecules in a burning flame for detecting their presence. However, the third detector 39 could naturally be any desired detector. Preferably the third detector is capable of receiving and analysing a continuous flow of a carrier medium conveying the sample. Examples of detectors usable as the third detector includes, but is not limited to, UV, IR, Fluorecence, SEM, X-ray, FID, etc.

Figure 14A:
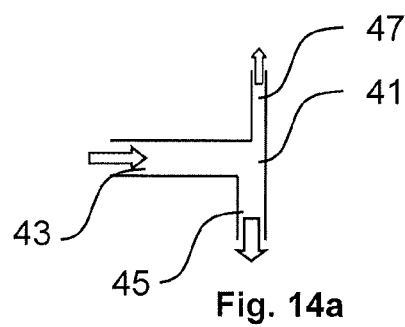

In FIG. 14a one example of a passive sample dividing member is shown. The sample dividing member 41 comprises an inlet 43 for receiving a chemical sample. The sample may be received as a one coherent body of material, or may preferably be received spread out in a carrier medium, such as inside a carrier gas.

The sample dividing member 41 further comprises a first outlet 45 arranged to connect the dividing member to a first detector, and a second outlet 47 connected with a second detector. The second outlet has a narrower diameter than the first outlet. Hence the pressure drop for a gas stream passing through the second outlet 47 is higher than when passing through the first outlet 45. Hence, the sample will be divided into a first sample part, having a high flow, and a second sample part, having a low flow. The outlets may be replaceable, wherein it is possible for an operator to change the dividing ratio between the first and second sample parts by changing the outlets for pipes with different dimensions.

Figure 14B:
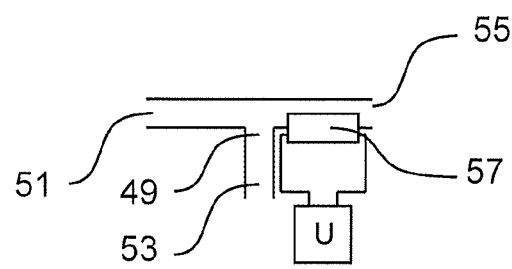

In FIG. 14b one example of an active sample dividing member 49 is shown. The sample dividing member comprises an inlet 51 and two outlets 53, 55 as previously described. The sample dividing member 49 further comprises an adjustment member 57 for adjusting the sample dividing ratio between the first and the second outlet. In this example the adjustment member 57 comprises a piezoelectric element restricting the diameter of the first outlet. By applying different voltages across the piezoelectric element the width of the element changes, wherein the sample dividing ratio of the dividing member may be controlled.

Figure 14C:
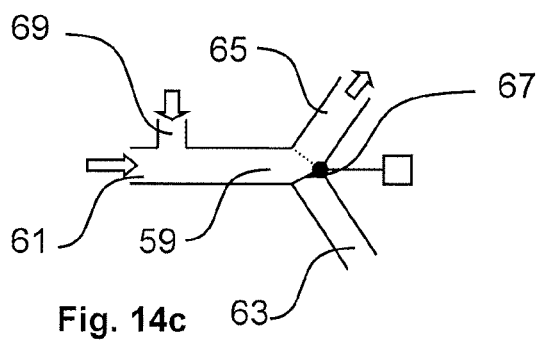

In FIG. 14c another example of an active sample dividing member 59 comprising an inlet 61 and a first 63 and a second 65 outlet is shown. The dividing member comprises an adjustment member 67 in the form of a shutter which is actuated to cover one of the outlets. By changing the time duration with which the outlets are covered it is possible to control the dividing ratio between the first and the second sample parts.

The sample dividing member further comprises an inert gas inlet 69 for receiving an inert gas into the dividing member 59. The inert gas may protect the dividing member 59 from air leaking into the dividing member, and/or may give the carrier flow an extra boost to increase the speed of the flow.

Figure 14D:
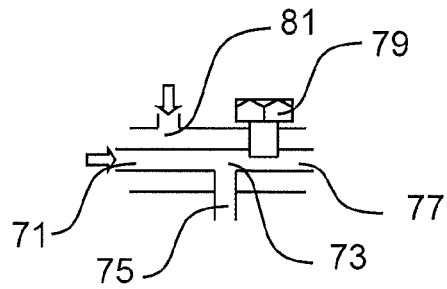

In FIG. 14d another example of a sample dividing member 71 comprising an inlet 73 and a first 75 and second 77 outlet is shown. The sample dividing member comprises an adjustment member 79 in the form of a screw, restricting the diameter of the second outlet. Hence by screwing the screw out or in, the diameter and thus the dividing ratio between the first and the second sample parts may be actuated.

The sample dividing member 71 further comprises a surrounding pipe 81 for conducting an inert gas around the dividing member 71. The inert gas may then protect the dividing member against air leaking into the dividing member, which otherwise could contaminate the sample.

Other forms of sample dividing members may be constructed by a man skilled in the art of pipes and chemical flows, or by a chemist or engineer skilled in the art of devices for dividing chemical substances into two parts. Further examples of dividing members include devices for gas flow regulation, glass capillaries, valves, and manual, electric, magnetic or hydraulic actuation. Inspiration may also be found from the construction of splitters, which are used in the prior art for injecting samples into mass spectrometers.

In FIG. 15 one example of a method according to the invention is shown. The method may be performed on a chemical analysation device as described above. The analysing parts of the method may also be effected by a computer program product comprising a computer program adapted to induce a computer to perform the steps when executed thereon. The computer may also exert computerized control over the analysation device when performing the method.

In a first step 83 the method comprises receiving a chemical sample comprising at least one compound to be analysed in a sample receiver. The method further comprises injecting the received chemical sample into a carrier gas flow for transportation of the sample.

In a second step 85 the method comprises inducing a separation of the compounds in the sample in a separator. In this example the separation step comprises inducing a separation of the compounds in the sample in a chromatograph, in this example in a gas chromatograph. Hence the compounds in the sample end up at different locations within the carrier gas stream, so that the different types of compounds reaches the detectors at different times.

In a third step 87 the method comprises dividing the received chemical sample into at least a first and a second sample parts in a sample dividing member. The method further comprises forwarding the first sample part into a first ionizer and further to a first detector, and forwarding the second sample part into a second ionizer and further to a second detector.

In the following the steps performed in relation to the first and the second sample parts are described separately for ease of understanding, however, the steps are in this example performed in parallel and simultaneously.

In a fourth step 89 the method comprises ionizing the first sample part in a first ionizer. In this example the method comprises ionizing the compound to be analysed in the first sample part in the first ionizer so that at least a majority of the ionized molecules of the compound to be analysed remain intact. This ionization may be performed with any known or future ionizer having the ability to ionize the compound so that the molecules remain intact. Preferably the method comprises exciting an inert molecule and bringing the inert, excited molecule in contact with the compound to be analysed.

In a fifth step 91 the method comprises detecting and/or analysing the ionized portions of the at least one compound to be analysed in the first sample part with a first detector. In this example the first detector comprises a mass spectrometer. The fifth step further comprises generating a first set of measurement data based on the analysis. In this example the first set of measurement data thus comprises information on mass/charge measured on a first sample part of the chemical sample. The data further comprises information acquired from measurements on molecules ionized so that the molecules remained intact.

In a sixth step 93 the method comprises receiving the first set of measurement data from the first detector in a computer, and fitting the first set of measurement data with information in a first database comprising a library with information on molecules and associated mass/charge values. In this example the method comprises fitting the first set of measurement data with information in a first database comprising a library with previously stored measurement values on intact molecules. The method further comprises estimating the quality of the fit and discarding the fit if it is outside a specified confidence interval.

Due to the separation in step 2 the compounds in the sample may arrive at different times to the detector. Hence the fourth to sixth steps are repeated continuously until it is believed that all compounds in the sample has reached the detector.

In a seventh step 95, and in parallel with step four, the method further comprises ionizing the second sample part in a second ionizer. The method comprises ionizing the sample so that at least a majority of the ionized molecules of the compound to be analysed are fragmented.

In an eight step 97 the method comprises detecting and/or analysing the at least one compound to be analysed in the second sample part with a second detector. In this example the method comprises detecting and/or analysing the ionized portions of the at least one compound to be analysed in a mass spectrometer. The eight step further comprises generating a second set of measurement data based on the analysis. The second set of measurement data thus comprises information on mass/charge values for the fragments of the compound, along with information on the abundance of the fragments.

In a ninth step 99 the method comprises receiving the second set of measurement data from a second detector, and fitting the second set of measurement data with information in a second database comprising a library with information on molecules and associated measurement values. In this example the library comprises previously stored measurement values on molecular fragments. Examples of steps that may be performed in the analysis comprises identifying a fragment of the compound to be analysed as a measured peak within the m/z-spectrum, identifying atoms contained within a fragment from a fit of a measured weight of the fragment with stored data on atomic and/or common fragment weights, and identifying functional groups within a fragment.

The steps seven to nine are in this example performed in parallel with the steps four to six. However, the steps six and nine may also be performed in combination and also in combination with step ten below.

In a tenth step 101 the method comprises combining the results from the first and second fits of the first and second sets of data to discern the identity, quantity, state and/or characteristics of a compound to be analysed within the chemical sample. The method comprises combining the results from the first and second fits in step six and nine to increase the determining, resolving and narrowing power when discerning the identity of the at least one compound to be analysed within the chemical sample. Thus the method comprises identifying any molecules having data stored in the first and the second databases that fits both the first and the second sets of measurement data.

In particular the tenth step may comprise receiving information on molecular weight for the compound to be analysed from a first detector comprising a mass spectrometer, and receiving information on molecular weight for the fragments of the compound to be analysed from a second detector comprising a mass spectrometer. The method may also comprise estimating the quantity and/or concentration of a molecule in the sample based on the second set of measurement data.

In an eleventh step 103 the method comprises presenting information on identified molecules and/or fragments to an operator, and in particular presenting information on a screen, such as on a computer screen.

If necessary the method may also comprise changing or tweaking time scales and time displacement for any graphs or other data obtained from the first and second detectors. Thus an operator may provide input so that events in the two sets of measurement data are correctly correlated with each other, wherein the analysis may be improved. The two databases comprising the libraries of information may also be present as one single database, or as several different databases. The fitting of measurement data to may be done with a least square method or any other known or new method for fitting data, such as splines, etc. The analysis may also comprise a search through a database rather than fitting values. Furthermore, an operator may provide input for limiting the analysis based on knowledge of the sample.

The invention is not limited to the examples shown but may be varied freely within the framework of the following claims. In particular, a feature presented with one embodiment or example may freely be combined or transferred to the other embodiments or examples.

III. The present invention further discloses a method for analyzing interactions between compounds of interest in a microfluidic electrocapture device and calculating binding coefficients between said compounds.

The compounds studied in the context of the present invention are termed "analytes" and "charged molecules". The only difference between analytes and charged molecules is that the charged molecules must have a net electric charge, either positive or negative, while the analytes may or may not have a net electric charge.

The invention enables analyzing molecular interactions in a liquid phase without the need for immobilization of a charged molecule to a solid support. The charged molecule is instead captured at a spot in a flow stream by means of a combination of an electric force and a hydrodynamic force applied to the flowing electrolytic medium. Since the charged molecule is not bound to any kind of support, all of its three-dimensional structure is intact and available for interactions with other molecules. Thereby, some of the drawbacks of the prior art may be avoided.

The method disclosed herein may be used to study whether a charged molecule of interest and an analyte of interest bind to each other. If they bind, the strength of the binding between the two analytes may be determined. Further, the binding site on the respective compound may be detected if each of the compounds is a molecule having a limited number of possible binding sites. Therefore, complex molecules will need to be separated into fragments before performing such a detection of the binding site.

The invention relates to a method for analyzing interactions between analytes and charged molecules travelling in an electrolytic flow stream through an electrically non-conductive channel, comprising at least one anode and at least one cathode individually separated from said channel, but in electrical contact with said flow stream by a conductive ion selective semi-permeable membrane. Said membrane permits the selective passage of either negatively or positively charged ions. This interferes with the normal circulation of ions towards the respective electrode, thereby accumulating ions inside the channel that are not allowed to pass through the ion selective membrane. By this means, at least two zones are generated, having different ionic strength, conductivity and local electric field strength. By modifying the selectivity of the ion-selective membrane (cation- or anion-selective) and/or the position of the anode and cathode (upstream or downstream), either i) the zone with lower electric field strength is situated upstream from the one with higher electric field strength; and a hydrodynamic force is applied to ions attracted by the electrode situated upstream, which is greater than and opposed to the electrical force generated on a charged molecule of interest situated at the zone with lower local electric field strength; thereby pushing the charged molecule of interest downstream towards the zone with a higher electric field strength, and lower than and opposed to the electrical force generated in the zone with higher electric field strength, resulting in the charged molecule being pushed back again upstream towards the zone with lower electric field strength; whereby the process is repeated, thereby immobilizing the ions between the zones with different electric field strengths; or ii) the zone with higher electric field strength is situated upstream from the one with lower electric field strength; whereby a charged molecule which is attracted by the upstream electrode and pulled with an electrical force greater than the hydrodynamic force of the flow stream, is not allowed to pass through the ion selective membrane but will be retained on the surface of the membrane.

The method according to the invention is performed by use of a so-called electrocapture device comprising at least one channel (1) built into an electrically non-conductive material, and at least one inlet (2) and one outlet (3) into said channel (1) for injection and exit of an electrolytic medium, and a system providing a continuous flow of said medium into said channel, and at least one anode (4) and at least one cathode (5), wherein said electrodes (4, 5) are individually separated from said channel (1), but in electrical contact with said electrolytic medium by a conductive membrane (6) each. Said membranes (6) are ion selective membranes, which permit the selective passage of certain charged ions or molecules and blockade of others. The ion selective membranes may be cation selective or anion selective. The channel may have any form and be arranged in any direction. Thus, the channel may be substantially vertical such as a substantially vertical column. Alternatively, the channel may be substantially horizontal. One or more channels may be present. Thus, one or more channels may be arranged in a substantially planar device.

Several electrodes and corresponding ion selective semipermeable membranes may be provided in the channel. Further, several channels can be arranged in the same electrical non-conductive material.

The electrocapture device comprises a microfluidic system, and may be incorporated into either of two basic microfluidic platforms, i.e. a capillary format or planar structures.

The hydrodynamic flow stream applied in the microfluidic device according to the method of the invention may be produced by a pump, gravity flow, gas or air pressure, centrifugal force or by electroosmosis. While these methods are preferred, any other method giving low flow rates (µL, nL or pL per min) may be used in the present invention.

An electrocapture device useful for carrying out the method according to the present invention is described in further detail in a previous PCT application having the publication number WO 2004/056697.

In one aspect of the invention, a method is disclosed for analyzing interactions between at least one analyte and at least one charged molecule, comprising
(a) providing a continuous flow of an electrolytic medium in a first electrically non-conductive channel;
(b) applying a voltage to said medium flowing through said channel by means of at least one anode and at least one cathode, individually separated from said channel but in electrical contact with said flowing medium by a conductive semi-permeable membrane;
(c) injecting said analyte into said electrolytic medium;
(d) allowing said analyte to flow through and exit said first channel;
(e) detecting said analyte or after its exit from the channel and measuring its retention time in said first channel;
(f) injecting at least one charged molecule into said electrolytic medium in a second electrically non-conductive channel;
(g) capturing said charged molecule by means of a combination of an electric force generated by the voltage applied between said electrodes, and a hydrodynamic force applied to the flowing electrolytic medium;
(h) injecting a further amount of said analyte into the electrolytic medium in said second channel;
(i) bringing said analyte into contact with said captured charged molecule whereby the analyte will be retarded proportionally to its interaction with the captured charged molecule;
(j) optionally, if said analyte and captured charged molecule interact strongly, modifying the applied flow rate and/or electrical field and/or by changing the electrolytic medium to a medium with a different ionic strength, pH or conductivity to weaken the interaction between the captured charged molecule and the analyte;
(k) allowing said analyte and/or said charged molecule to exit said second channel;
(l) detecting the analyte and/or charged molecule and/or a complex formed of the charged molecule and the analyte on or after their respective exit from said second channel, and measuring their respective retention times in the channel;
(m) calculating at least one binding coefficient, or binding coefficient related parameter, of the analyte with respect to the charged molecule based on a comparison of retention times in steps (e) and (l).

The steps (a)-(e) and (f)-(l), respectively, may be performed substantially at the same time, i.e. in parallel, or consecutively, i.e. in series. If they are performed in series, the first and second electrically non-conductive channel may physically be the same electrically non-conductive channel.

The retention time represents the time it takes for an analyte to pass from the inlet of the channel to the detector. The retention time of an analyte is defined as the elapsed time between the time of injection of said analyte and the time of elution of the peak maximum of said analyte when detected by the detector. In the present invention, the retention time can be used to estimate the magnitude of the interaction or binding of the analyte to the charged molecule. For example, an analyte with a higher retention time will have a higher binding capability than another analyte with a lower retention time. A useful terminology derived from the retention time is called "corrected retention time", and is defined as the retention time subtracted by the retention time of an analyte passing through the channel without being retarded, i.e. passing through at the flow rate of the electrolytic medium. The corrected retention time can be used to correlate the binding strengths of different analytes. For example, an analyte with a high corrected retention time will have a higher binding capability than another analyte with a low corrected retention time.

In medicinal chemistry and pharmacology, a binding coefficient is a quantity representing the extent to which a chemical compound will bind to a macromolecule (Schurr J M, Rangel D P, Aragon S R. (2005) "A Contribution to the Theory of Preferential Interaction Coefficients." Biophysical Journal. 89:2258-2276). The retention time can be converted into the binding coefficient by calibrating the invention with analytes with known binding coefficients. By obtaining the retention times of the analytes of interest with known binding coefficients, these retention times could be assigned to the corresponding binding coefficients, and by this means calibrating the invention to obtain the binding coefficient via the retention time.

In a further aspect, the present invention relates to a method for performing separations of analytes of interest based on different binding affinities of said analytes of interest for the captured charged molecules. In this embodiment the captured charged molecule might comprise a molecule that it is known to have certain degree of affinity for the analyte of interest, and by this means, it is possible to use this principle to separate molecules. For example (non-limited example) a molecule as dodecyl sulphate (or molecules with a molecular formula $C_nH_{2n+a}SO_4$ where n is 2, 4, 6, 8) could be captured in order to separate analytes of interest having different affinity for the dodecyl-chain. A variation of this embodiment might comprise the change of pH and or solvent polarity (different composition of methanol and/or acetonitrile) in order to promote and/or enhance the separation of the analytes of interest. Other charged molecules might be electro-captured, positively or negatively charged molecule having molecular structures chosen to promote the separation of the molecules of interest according to the binding affinities (and/or solubility) of the analyte of interest for the captured charged molecule of interest.

In a preferred embodiment, the methods according to the invention permit analyzing a library of analytes with respect to interactions of all the analytes in the library with at least one charged molecule. Thus, a screening or separation of a library of a vast number of analytes may be performed by use of the electrocapture device.

In a specific embodiment, the analytical instrument performing the detection and measurement of analytes and charged molecules consists of a mass spectrometer. The mass spectrometer could be connected online or off line with the electrocapture device.

In one embodiment, the mass spectrometer has an electrospray ion source.

In a further embodiment, the mass spectrometer has dual or multiple electrospray ion sources coupled in parallel and data is sampled from only one of the needles at a time by switching between said electrospray ion sources. This may be accomplished by using a MUX-system (patent application filed by Waters/Micromass) using a baffle or screen that can be moved in front of one electrospray ion source such that the mass spectrometer only samples data from the other and vice versa. Another system could use moveable spray needles, which could be moved back and forth in front of the sample hole of the electrospray source of the mass spectrometer. The parallel system has no cross-talk between the different electrospray ion sources and data from the individual sources is acquired in separate data files for further comparison and post-processing. After comparing the two or more sets of data, including retention times, the differences in retention time may be used to calculate binding coefficients of the analytes.

In one embodiment, the mass spectrometer has a matrix-assisted laser desorption ion (MALDI) source.

In another embodiment, the analytical instrument performing the detection and measurement of analytes and charged molecules is a UV detector.

In one embodiment, the analytical instrument performing the detection and measurement of analytes and charged molecules consists of a mass spectrometer and a UV detector.

In an alternative embodiment, the method according to the present invention may be combined with a hydrogen/deuterium exchange cell which can detect conformational changes upon the binding of putative interacting analytes of interest. In this embodiment, the analyte of interest is deuterated by using the deuterating cell downstream from the outlet of the electrocapture cell. In this case, the deuteration will occur when the molecule of interest is released from the electrocapture cell. In another embodiment, the analyte of interest is deuterated by using the deuterating cell between the electrocapture membranes.

The invention claimed is:

1. Apparatus for performing in-solution hydrogen/deuterium exchange on analytes of interest comprising:

a deuteration cell consisting of at least one sample solution channel which functions as a conduit for a liquid which contains an analyte of interest, at least one deuterated solution channel which functions as a conduit for another liquid, and an ion-selective membrane interposed between said at least one sample solution channel and said at least one deuterated solution channel, said ion-selective membrane being disposed in a mixing region and separating the at least one sample solution channel from the at least one deuterated solution channel, the ion-selective membrane having a first side proximate the at least one sample solution channel and a second side proximate the at least one deuterated solution channel, the ion-selective membrane being semi-permeable such that a deuterated solvent liquid is configured to pass through said ion-selective membrane from said at least one deuterated solution channel into said at least one sample solution channel, wherein the passage of the deuterated solvent liquid through the ion-selective membrane into the at least one sample solution channel is configured to promote an exchange of hydrogen atoms for deuterium atoms into a molecular structure of analytes of interest located in said at least one sample solution channel, during which said sample solution channel is configured to operate at a temperature which is not greater than ambient temperature, a first device which directs a portion of a population of analytes of interest from the mixing region into a vacuum chamber, wherein said first device comprises an injection valve, which is configured to allow for the injection of discrete amount of the analytes of interest into a chromatographic column, and wherein the outlet of the chromatographic column is connected to online electrospray mass spectrometry with electrospray ionization, and a second device which conducts mass to charge analysis on a portion of said analytes transferred into said vacuum chamber.

2. The apparatus according to claim 1, further comprising an injector configured to inject the analytes of interest subjected to deuteration into the mixing region using different flow rates in order to achieve different incubation times.

3. The apparatus according to claim 2, wherein the injector is configured to inject the analytes of interest subjected to deuteration into the mixing region using flow rates in the range of from one nanoliter to one microliter per minute in order to increase the incubation time for the hydrogen/deuterium exchange reaction.

4. The apparatus according to claim 2, wherein, the injector is configured to inject the analyte of interest subjected to deuteration into the mixing region using flow rates of at least one microliter per minute in order to decrease the incubation time for the hydrogen/deuterium exchange reaction.

5. The apparatus according to claim 1, wherein said at least one deuterated solution channel contains an undeuterated solvent at the time when the analyte of interest is injected into the mixing region;

the analyte of interest is stopped or has a flow rate in the range of from one nanoliter to one microliter per minute in the mixing region;

the solution in said at least one deuterated solution channel is changed to a deuterated solvent; thereby allowing the exchange of hydrogen atoms for deuterium atoms into the molecular structure of the analytes of interest located in said at least one sample solution channel.

6. The apparatus according to claim 5, wherein an incubation time of the hydrogen deuterium exchange reaction of an analyte of interest in the mixing region comprises the time between the change of the undeuterated solvent for a deuterated solvent and the time at which the analyte of interest is eluted from the mixing region.

7. The apparatus according to claim 6, wherein the incubation time of the hydrogen deuterium exchange reaction is changed by changing the residence time of the analytes of interest into the mixing region.

8. The apparatus according to claim 1, wherein the analyte of interest subjected to deuteration is a protein and/or protein/protein complex and/or protein/drug complex and/or protein/DNA complex and/or protein/RNA and/or protein/carbohydrate complex and/or protein/lipid complex.

9. The apparatus according to claim 8, further comprising a proteolytic enzyme which enables digestion of the deuterated protein prior to submission of the resulting deuterated proteolytic fragments to the mass to charge analysis, and obtaining structural information about binding sites and/or secondary and/or tertiary and/or quaternary structural information about the protein.

10. The apparatus according to claim 1, further comprising an electrocapture system arranged after said deuteration cell and that is configured to receive the analytes of interest from the mixing region before said first device directs the portion of the population of analytes of interest from the mixing region into the vacuum chamber.

11. The apparatus according to claim 10, wherein said electrocapture system includes at least one sample channel configured for receiving the analytes of interest, at least one electrolyte reservoir including an electrode, and a semipermeable membrane that separates said at least one sample channel from said electrode of said at least one electrolyte, said electrode of said at least one electrolyte reservoir being the first electrode in a flow path of sample solution from a source thereof through said at least one sample solution channel of said deuteration cell and through said at least one sample channel of said electrocapture system.

12. The apparatus according to claim 10, wherein said electrocapture system includes first and second sample channels configured for receiving the analytes of interest, an electrolyte reservoir including first and second electrodes, a first semipermeable membrane that separates said first sample channel from said first electrode, and a second semipermeable membrane that separates said second sample channel from second electrode, said first electrode of said electrolyte reservoir being the first electrode in a flow path of sample solution from a source thereof through said at least one sample solution channel of said deuteration cell and through said first sample channel of said electrocapture system.

13. The apparatus according to claim 1, wherein said deuteration cell does not comprise means for generating an electric field or an electric potential across said ion-selective membrane.

14. The apparatus according to claim 1, wherein said deuteration cell is made of electrically non-conductive plastic.

15. The apparatus according to claim 1, wherein said deuteration cell is made of electrically non-conductive material.

16. The apparatus according to claim 1, further comprising an injector arranged after said deuteration cell and that is configured to direct acidified solution into sample solution being outlet from said deuteration cell before said first device directs the portion of the population of analytes of interest from the mixing region into the vacuum chamber.

17. The apparatus according to claim 16, further comprising a T-connector coupled to said injector and through which the acidified solution is directed by said injector into communication with a flow channel through which sample solution outlet from said deuteration cell flows.

* * * * *